(12) United States Patent
Sawadaishi et al.

(10) Patent No.: US 7,381,798 B2
(45) Date of Patent: Jun. 3, 2008

(54) RECOMBINANT ANTIBODY RECOGNIZING DIOXIN AND GENE ENCODING THE ANTIBODY

(75) Inventors: Kazuyuki Sawadaishi, Kyoto (JP); Keiichi Higano, Kyoto (JP); Chiwa Kataoka, Kyoto (JP)

(73) Assignee: Kyoto Electronics Manufacturing Co., Ltd., Kyoto (JP)

( * ) Notice: Subject to any disclaimer, the term of this patent is extended or adjusted under 35 U.S.C. 154(b) by 195 days.

(21) Appl. No.: 10/550,951

(22) PCT Filed: Mar. 26, 2004

(86) PCT No.: PCT/JP2004/004355

§ 371 (c)(1),
(2), (4) Date: Jun. 14, 2006

(87) PCT Pub. No.: WO2004/087764

PCT Pub. Date: Oct. 14, 2004

(65) Prior Publication Data

US 2006/0269977 A1 Nov. 30, 2006

(30) Foreign Application Priority Data

Mar. 28, 2003 (JP) ............................. 2003-091663

(51) Int. Cl.
*G01N 33/53* (2006.01)
*C12P 21/04* (2006.01)
*C12P 21/08* (2006.01)
*C12N 1/20* (2006.01)
*C12N 5/06* (2006.01)
*C07K 16/00* (2006.01)
*C07H 21/04* (2006.01)

(52) U.S. Cl. .................. 530/387.1; 435/7.1; 435/69.6; 435/252.3; 435/326; 530/387.3; 530/388.1; 536/23.53

(58) Field of Classification Search ...................... None
See application file for complete search history.

(56) References Cited

U.S. PATENT DOCUMENTS 4,798,807 A 1/1989 Vanderlaan et al. ........ 436/548

FOREIGN PATENT DOCUMENTS

JP 2002-119279 4/2002
JP 2002-228660 8/2002
JP 2002-340882 11/2002

OTHER PUBLICATIONS

Takasuga, et al., "11th Symposium on Environmental Chemistry, Program and Abstracts", 2002, pp. 136-137.
Lefranc, M.-P., et al., "IMGT, the International Immunogenetics Database", Nucleic Acids Research, vol. 27, No. 1, 1999, pp. 209-212.
Ruiz, M., et al., "IMGT, the International Immunogenetics Database", Nucleic Acids Research, vol. 28, No. 1, 2000, pp. 219-221.
Lefranc, M.-P., "IMGT, the International Immunogenetics Database", Nucleic Acids Research, vol. 29, No. 1, 2001, pp. 207-209.
Stanker, L.H. et al., "Monoclonal antibodies for dioxin: antibody characterization and assay development", Toxicology 1987, vol. 45, No. 3, pp. 229-243.
Naoya Omura et al., "Dioxin-rui no Jinsoku Kan-i Sokutei Men-eki Sokutei (Immunoassay) -ho", Environmental Management, Mar. 10, 2003, vol. 39, No. 3, pp. 251-256.
Omura, N., et al., "Dioxin-rui no Jinsoku Kan-I Sokutei Men-eki Sokutei (Immunoassay)-ho", Environmental Management, Mar. 10, 2003, vol. 39, No. 3, pp. 251-256.
Recinos III, A., et al., "Sequences of cDNAs encoding immunoglobulin heavy- and light- chain variable regions from two anti-dioxin monoclonal antibodies [Gene 149 (1994) 385-386]", Gene, Vol. 158, No. 2, Jun. 9, 1995, pp. 311-312.
Huwe, J.K., et a., "On the isolation of polychlorinated dibenzo-p-dioxins and furans from serum samples using immunoaffinity chromatography prior to high-resolution gas chromatography-mass spectrometry", Journal of chromatography B, vol. 757, No. 2, (2001), pp. 285-293.
Shelver, W.L., et al., "Comparison of immunoaffinity column recovery patterns of polychlorinated dibenzo-p-dioxins/polychlorinated dibenzofurans on columns generated with different monoclonal antibody clones and polyclonal antibodies", Analytica Chimica Acta, vol. 457, No. 2, (2002), pp. 199-209.

*Primary Examiner*—Maher M. Haddad
*Assistant Examiner*—Chun Dahle
(74) *Attorney, Agent, or Firm*—Bacon & Thomas, PLLC

(57) ABSTRACT

The present invention relates to a novel recombinant antibody having a binding activity to 2,3,4,7,8-pentachlorodibenzofuran (2,3,4,7,8-PeCDF), a gene encoding its amino acid sequence, a vector incorporating said gene, a transformant transformed with said vector, a process for preparing said recombinant antibody, and methods for immunologically capturing and determining 2,3,4,7,8-PeCDF using said recombinant antibody. Using the recombinant antibody according to the present invention, it is possible to capture and determine dioxins, in particular, 2,3,4,7,8-PeCDF by an immunological technique in a rapid, convenient, and highly sensitive manner.

9 Claims, 11 Drawing Sheets

```
  1  GAA GTG AAG CTG GTG GAG TCT GGG GGA GGC TTA GTG AAG CCT GGA GGG TCC CTG AAA CTC   60
  1  Glu Val Lys Leu Val Glu Ser Gly Gly Gly Leu Val Lys Pro Gly Gly Ser Leu Lys Leu   20

61  TCC TGT GCA GCC TCT GGA TTC ACT TTC AGT TCC TAT GCC ATG TCT TGG GTT CGC CAG ACT  120
 21  Ser Cys Ala Ala Ser Gly Phe Thr Phe Ser Ser Tyr Ala Met Ser Trp Val Arg Gln Thr   40
                     ————————CDR1-IMGT————————

121  CCA GAG AAG AGG CTG GAG TGG GTC GCA TCC TTT AGT AAT GGT GGT ATC ACC TAC TAT CCA  180
 41  Pro Glu Lys Arg Leu Glu Trp Val Ala Ser Phe Ser Asn Gly Gly Ile Thr Tyr Tyr Pro   60
                                 ————————CDR2-IMGT————————

181  GAC AGT GTG AAG GGC CGA TTC ACC ATC TCC AGA GAT AAT GCC AGG AAC ATC CTG TAC CTG  240
 61  Asp Ser Val Lys Gly Arg Phe Thr Ile Ser Arg Asp Asn Ala Arg Asn Ile Leu Tyr Leu   80

241  CAA ATG ACC AGT CTG AGG TCT GAG GAC ACG GCC ATT TAT TAC TGT GCA AGA GGC TAT GGT  300
 81  Gln Met Thr Ser Leu Arg Ser Glu Asp Thr Ala Ile Tyr Tyr Cys Ala Arg Gly Tyr Gly  100
                                                             ————————CDR3-IMGT

301  CCT GCT TAC TGG GGC CAA GGG ACT CTG GTC ACT GTC TCT GCA                          342
101  Pro Ala Tyr Trp Gly Gln Gly Thr Leu Val Thr Val Ser Ala                          114
```

```
  1  CAG GCT GTT GTG ACT CAG GAA TCT GCA CTC ACC ACA TCA CCT GGT GAA ACA GTC ACA CTC   60
  1  Gln Ala Val Val Thr Gln Glu Ser Ala Leu Thr Thr Ser Pro Gly Glu Thr Val Thr Leu   20

61  ACT TGT CGC TCA AGT ACT GGG GCT GTT ACA ACT CTT AAC TAT GCC AAC TGG GTC CAA GAA  120
 21  Thr Cys Arg Ser Ser Thr Gly Ala Val Thr Thr Leu Asn Tyr Ala Asn Trp Val Gln Glu   40
                      ————————CDR1-IMGT————————

121  AAA CCA GAT CAT TTA TTC ACT GGT CTA ATA GGT AAT ACC AAC AAC CGA GCT CCA GGT GTT  180
 41  Lys Pro Asp His Leu Phe Thr Gly Leu Ile Gly Asn Thr Asn Asn Arg Ala Pro Gly Val   60
                                     -CDR2-IMGT-

181  CCT GCC AGA TTC TCA GGC TCC CTG ATT GGA GAC AAG GCT GCC CTC ACC ATC ACA GGG GCA  240
 61  Pro Ala Arg Phe Ser Gly Ser Leu Ile Gly Asp Lys Ala Ala Leu Thr Ile Thr Gly Ala   80

241  CAG ACT GAG GAT GAG GCA ATA TAT TTC TGT GCT CTA TGG TAC AGC AAC CAT TTG GTG TTC  300
 81  Gln Thr Glu Asp Glu Ala Ile Tyr Phe Cys Ala Leu Trp Tyr Ser Asn His Leu Val Phe  100
                                                     ————————CDR3-IMGT————————

301  GGT GGA GGA ACC AAA CTG ACT GTC CTA GGC                                          330
101  Gly Gly Gly Thr Lys Leu Thr Val Leu Gly                                          110
```

| 1 | GAT GTA CAG CTT CAG GAG TCA GGA CCT GGC CTC GTG AAA CCT TCT CAG TCT CTG TCT CTC | 60 |
| 1 | Asp Val Gln Leu Gln Glu Ser Gly Pro Gly Leu Val Lys Pro Ser Gln Ser Leu Ser Leu | 20 |

| 61 | ACC TGT TCT GTC ACT GGC TAC TCC ATC ACC AGT GGC TTT TAC TGG AAC TGG ATC CGG CAG | 120 |
| 21 | Thr Cys Ser Val Thr Gly Tyr Ser Ile Thr Ser Gly Phe Tyr Trp Asn Trp Ile Arg Gln | 40 |

————————CDR1-IMGT————————

| 121 | TTT CCA GGA AAC AAA CTG GAA TGG ATG GGC TAC ATA AGC TAC GAC GGT TAC AAT AAT TAC | 180 |
| 41 | Phe Pro Gly Asn Lys Leu Glu Trp Met Gly Tyr Ile Ser Tyr Asp Gly Tyr Asn Asn Tyr | 60 |

————————CDR2-IMGT————————

| 181 | AAC CCA TTT CTC AAA AAT CGA GTG TCC ATC ACT CGT GAC ACA TCT GAG AAC CAG TTT TTC | 240 |
| 61 | Asn Pro Phe Leu Lys Asn Arg Val Ser Ile Thr Arg Asp Thr Ser Glu Asn Gln Phe Phe | 80 |

| 241 | CTG AAG TTG CAT TCT GTG ACT ACT GAG GAC ACA GCT ACA TAT TAC TGT GTA AGT TAC GGT | 300 |
| 81 | Leu Lys Leu His Ser Val Thr Thr Glu Asp Thr Ala Thr Tyr Tyr Cys Val Ser Tyr Gly | 100 |

| 301 | AGT CGG AGG GGA GTT ACC TAC TGG GGC CAA GGC ACC ACT CTC ACA GTC TCC TCA | 354 |
| 101 | Ser Arg Arg Gly Val Thr Tyr Trp Gly Gln Gly Thr Thr Leu Thr Val Ser Ser | 118 |

——CDR3-IMGT————————

| 1 | CAG GCT GTT GTG ACT CAG GAA TCT GCA CTC ACC ACA TCA CCT GGT GAA ACA GTC ACA CTC | 60 |
| 1 | Gln Ala Val Val Thr Gln Glu Ser Ala Leu Thr Thr Ser Pro Gly Glu Thr Val Thr Leu | 20 |

| 61 | ACT TGT CGC TCA AGT ACT GGG GCT GTT ACA ACT AGT AAC TAT GCC AAC TGG GTC CAA GAA | 120 |
| 21 | Thr Cys Arg Ser Ser Thr Gly Ala Val Thr Thr Ser Asn Tyr Ala Asn Trp Val Gln Glu | 40 |

————————CDR1-IMGT————————

| 121 | AAA CCA GAT CAT TTA TTC ACT GGT CTA ATA GGT AAT ACC AAC AAC GGA GCT CCA GGT GTT | 180 |
| 41 | Lys Pro Asp His Leu Phe Thr Gly Leu Ile Gly Asn Thr Asn Asn Arg Ala Pro Gly Val | 60 |

-CDR2-IMGT-

| 181 | CCT GCC AGA TTC TCT GGC TCC CTG ATT GGA GAC AAG GCT GCC CTC ACC ATC ACA GGG GCA | 240 |
| 61 | Pro Ala Arg Phe Ser Gly Ser Leu Ile Gly Asp Lys Ala Ala Leu Thr Ile Thr Gly Ala | 80 |

| 241 | CAG ACT GAG GAT GAG GCG ATA TAT TTC TGT GCT CTT TGG TAC AAC ACC CAT TTG GTG TTC | 300 |
| 81 | Gln Thr Glu Asp Glu Ala Ile Tyr Phe Cys Ala Leu Trp Tyr Asn Thr His Leu Val Phe | 100 |

————————CDR3-IMGT————————

| 301 | GGT GGA GGA ACC AGA CTG ACT GTC CTA GGC | 330 |
| 101 | Gly Gly Gly Thr Arg Leu Thr Val Leu Gly | 110 |

Fig. 5

Dx3860H L scFv

```
  1 GAA GTG AAG CTG GTG GAG TCC GGG GGA GGC TTA GTG AAG CCT GGA GGG TCC CTG AAA CTC   60
    CTT CAC TTC GAC CAC CTC AGG CCC CCT CCG AAT CAC TTC GGA CCT CCC AGG GAC TTT GAG
  1 Glu-Val-Lys-Leu-Val-Glu-Ser-Gly-Gly-Gly-Leu-Val-Lys-Pro-Gly-Gly-Ser-Leu-Lys-Leu   20
    VH→

61 TCC TGT GCA GCC TCT GGA TTC ACT TTC AGT TCC TAT GCC ATG TCT TGG GTT CGC CAG ACT  120
    AGG ACA CGT CGG AGA CCT AAG TGA AAG TCA AGG ATA CGG TAC AGA ACC CAA GCG GTC TGA
 21 Ser-Cys-Ala-Ala-Ser-Gly-Phe-Thr-Phe-Ser-Ser-Tyr-Ala-Met-Ser-Trp-Val-Arg-Gln-Thr   40

121 CCA GAG AAG AGG CTG GAG TGG GTC GCA TCC TTT AGT AAT GGT GGT ATC ACC TAC TAT CCA  180
    GGT CTC TTC TCC GAC CTC ACC CAG CGT AGG AAA TCA TTA CCA CCA TAG TGG ATG ATA GGT
 41 Pro-Glu-Lys-Arg-Leu-Glu-Trp-Val-Ala-Ser-Phe-Ser-Asn-Gly-Gly-Ile-Thr-Tyr-Tyr-Pro   60

181 GAC AGT GTG AAG GGC CGA TTC ACC ATC TCC AGA GAT AAT GCC AGG AAC ATC CTG TAC CTG  240
    CTG TCA CAC TTC CCG GCT AAG TGG TAG AGG TCT CTA TTA CGG TCC TTG TAG GAC ATG GAC
 61 Asp-Ser-Val-Lys-Gly-Arg-Phe-Thr-Ile-Ser-Arg-Asp-Asn-Ala-Arg-Asn-Ile-Leu-Tyr-Leu   80

241 CAA ATG ACC AGT CTG AGG TCT GAG GAC ACG GCC ATT TAT TAC TGT GCA AGA GGC TAT GGT  300
    GTT TAC TGG TCA GAC TCC AGA CTC CTG TGC CGG TAA ATA ATG ACA CGT TCT CCG ATA CCA
 81 Gln-Met-Thr-Ser-Leu-Arg-Ser-Glu-Asp-Thr-Ala-Ile-Tyr-Tyr-Cys-Ala-Arg-Gly-Tyr-Gly  100

301 CCT GCT TAC TGG GGC CAA GGT ACC CTG GTC ACT GTC TCT TCC GGA GGA GGC GGT TCA GGC  360
    GGA CGA ATG ACC CCG GTT CCA TGG GAC CAG TGA CAG AGA AGG CCT CCT CCG CCA AGT CCG
101 Pro-Ala-Tyr-Trp-Gly-Gln-Gly-Thr-Leu-Val-Thr-Val-Ser-Ser-Gly-Gly-Gly-Gly-Ser-Gly  120

361 GGA GGT GGC TCT GGC GGT GGC GGA TCC CAG GCT GTT GTG ACT CAG GAA TCT GCA CTC ACC  420
    CCT CCA CCG AGA CCG CCA CCG CCT AGG GTC CGA CAA CAC TGA GTC CTT AGA CGT GAG TGG
121 Gly-Gly-Gly-Ser-Gly-Gly-Gly-Gly-Ser-Gln-Ala-Val-Val-Thr-Gln-Glu-Ser-Ala-Leu-Thr  140
    Linker                              VL→

421 ACA TCA CCT GGT GAA ACA GTC ACA CTC ACT TGT CGC TCA AGT ACT GGG GCT GTT ACA ACT  480
    TGT AGT GGA CCA CTT TGT CAG TGT GAG TGA ACA GCG AGT TCA TGA CCC CGA CAA TGT TGA
141 Thr-Ser-Pro-Gly-Glu-Thr-Val-Thr-Leu-Thr-Cys-Arg-Ser-Ser-Thr-Gly-Ala-Val-Thr-Thr  160

481 CTT AAC TAT GCC AAC TGG GTC CAA GAA AAA CCA GAT CAT TTA TTC ACT GGT CTA ATA GGT  540
    GAA TTG ATA CGG TTG ACC CAG GTT CTT TTT GGT CTA GTA AAT AAG TGA CCA GAT TAT CCA
161 Leu-Asn-Tyr-Ala-Asn-Trp-Val-Gln-Glu-Lys-Pro-Asp-His-Leu-Phe-Thr-Gly-Leu-Ile-Gly  180

541 AAT ACC AAC AAC CGA GCT CCA GGT GTT CCT GCC AGA TTC TCA GGC TCC CTG ATT GGA GAC  600
    TTA TGG TTG TTG GCT CGA GGT CCA CAA GGA CGG TCT AAG AGT CCG AGG GAC TAA CCT CTG
181 Asn-Thr-Asn-Asn-Arg-Ala-Pro-Gly-Val-Pro-Ala-Arg-Phe-Ser-Gly-Ser-Leu-Ile-Gly-Asp  200

601 AAG GCT GCC CTC ACC ATC ACA GGG GCA CAG ACT GAG GAT GAG GCA ATA TAT TTC TGT GCT  660
    TTC CGA CGG GAG TGG TAG TGT CCC CGT GTC TGA CTC CTA CTC CGT TAT ATA AAG ACA CGA
201 Lys-Ala-Ala-Leu-Thr-Ile-Thr-Gly-Ala-Gln-Thr-Glu-Asp-Glu-Ala-Ile-Tyr-Phe-Cys-Ala  220

661 CTA TGG TAC AGC AAC CAT TTG GTG TTC GGT GGA GGA ACC AAA CTG ACT GTC CTA GGC       717
    GAT ACC ATG TCG TTG GTA AAC CAC AAG CCA CCT CCT TGG TTT GAC TGA CAG GAT CCG
221 Leu-Trp-Tyr-Ser-Asn-His-Leu-Val-Phe-Gly-Gly-Gly-Thr-Lys-Leu-Thr-Val-Leu-Gly      239
```

Fig. 6

Dx3860 L H scFv

```
  1 CAG GCT GTT GTG ACT CAG GAA TCT GCA CTC ACC ACA TCA CCT GGT GAA ACA GTC ACA CTC   60
    GTC CGA CAA CAC TGA GTC CTT AGA CGT GAG TGG TGT AGT GGA CCA CTT TGT CAG TGT GAG
  1 Gln-Ala-Val-Val-Thr-Gln-Glu-Ser-Ala-Leu-Thr-Thr-Ser-Pro-Gly-Glu-Thr-Val-Thr-Leu   20
    VL →

61 ACT TGT CGC TCA AGT ACT GGG GCT GTT ACA ACT CTT AAC TAT GCC AAC TGG GTC CAA GAA  120
    TGA ACA GCG AGT TCA TGA CCC CGA CAA TGT TGA GAA TTG ATA CGG TTG ACC CAG GTT CTT
 21 Thr-Cys-Arg-Ser-Ser-Thr-Gly-Ala-Val-Thr-Thr-Leu-Asn-Tyr-Ala-Asn-Trp-Val-Gln-Glu   40

121 AAA CCA GAT CAT TTA TTC ACT GGT CTA ATA GGT AAT ACC AAC AAC CGA GCT CCA GGT GTT  180
    TTT GGT CTA GTA AAT AAG TGA CCA GAT TAT CCA TTA TGG TTG TTG GCT CGA GGT CCA CAA
 41 Lys-Pro-Asp-His-Leu-Phe-Thr-Gly-Leu-Ile-Gly-Asn-Thr-Asn-Asn-Arg-Ala-Pro-Gly-Val   60

181 CCT GCC AGA TTC TCA GGC TCC CTG ATT GGA GAC AAG GCT GCC CTC ACC ATC ACA GGG GCA  240
    GGA CGG TCT AAG AGT CCG AGG GAC TAA CCT CTG TTC CGA CGG GAG TGG TAG TGT CCC CGT
 61 Pro-Ala-Arg-Phe-Ser-Gly-Ser-Leu-Ile-Gly-Asp-Lys-Ala-Ala-Leu-Thr-Ile-Thr-Gly-Ala   80

241 CAG ACT GAG GAT GAG GCA ATA TAT TTC TGT GCT CTA TGG TAC AGC AAC CAT TTG GTG TTC  300
    GTC TGA CTC CTA CTC CGT TAT ATA AAG ACA CGA GAT ACC ATG TCG TTG GTA AAC CAC AAG
 81 Gln-Thr-Glu-Asp-Glu-Ala-Ile-Tyr-Phe-Cys-Ala-Leu-Trp-Tyr-Ser-Asn-His-Leu-Val-Phe  100

301 GGT GGA GGA ACC AAA CTG ACT GTC CTA GGC TCC GGA GGA GGC GGT TCA GGC GGA GGT GGC  360
    CCA CCT CCT TGG TTT GAC TGA CAG GAT CCG AGG CCT CCT CCG CCA AGT CCG CCT CCA CCG
101 Gly-Gly-Gly-Thr-Lys-Leu-Thr-Val-Leu-Gly-Ser-Gly-Gly-Gly-Gly-Ser-Gly-Gly-Gly-Gly  120
                                              Linker 361 TCT GGC GGT GGC GGA TCC GAA GTG AAG CTG GTG GAG TCC GGG GGA GGC TTA GTG AAG CCT  420
    AGA CCG CCA CCG CCT AGG CTT CAC TTC GAC CAC CTC AGG CCC CCT CCG AAT CAC TTC GGA
121 Ser-Gly-Gly-Gly-Gly-Ser-Glu-Val-Lys-Leu-Val-Glu-Ser-Gly-Gly-Gly-Leu-Val-Lys-Pro  140
                         VH →

421 GGA GGG TCC CTG AAA CTC TCC TGT GCA GCC TCT GGA TTC ACT TTC AGT TCC TAT GCC ATG  480
    CCT CCC AGG GAC TTT GAG AGG ACA CGT CGG AGA CCT AAG TGA AAG TCA AGG ATA CGG TAC
141 Gly-Gly-Ser-Leu-Lys-Leu-Ser-Cys-Ala-Ala-Ser-Gly-Phe-Thr-Phe-Ser-Ser-Tyr-Ala-Met  160

481 TCT TGG GTT CGC CAG ACT CCA GAG AAG AGG CTG GAG TGG GTC GCA TCC TTT AGT AAT GGT  540
    AGA ACC CAA GCG GTC TGA GGT CTC TTC TCC GAC CTC ACC CAG CGT AGG AAA TCA TTA CCA
161 Ser-Trp-Val-Arg-Gln-Thr-Pro-Glu-Lys-Arg-Leu-Glu-Trp-Val-Ala-Ser-Phe-Ser-Asn-Gly  180

541 GGT ATC ACC TAC TAT CCA GAC AGT GTG AAG GGC CGA TTC ACC ATC TCC AGA GAT AAT GCC  600
    CCA TAG TGG ATG ATA GGT CTG TCA CAC TTC CCG GCT AAG TGG TAG AGG TCT CTA TTA CGG
181 Gly-Ile-Thr-Tyr-Tyr-Pro-Asp-Ser-Val-Lys-Gly-Arg-Phe-Thr-Ile-Ser-Arg-Asp-Asn-Ala  200

601 AGG AAC ATC CTG TAC CTG CAA ATG ACC AGT CTG AGG TCT GAG GAC ACG GCC ATT TAT TAC  660
    TCC TTG TAG GAC ATG GAC GTT TAC TGG TCA GAC TCC AGA CTC CTG TGC CGG TAA ATA ATG
201 Arg-Asn-Ile-Leu-Tyr-Leu-Gln-Met-Thr-Ser-Leu-Arg-Ser-Glu-Asp-Thr-Ala-Ile-Tyr-Tyr  220

661 TGT GCA AGA GGC TAT GGT CCT GCT TAC TGG GGC CAA GGG ACT CTG GTC ACT GTC TCT GCA  720
    ACA CGT TCT CCG ATA CCA GGA CGA ATG ACC CCG GTT CCC TGA GAC CAG TGA CAG AGA CGT
221 Cys-Ala-Arg-Gly-Tyr-Gly-Pro-Ala-Tyr-Trp-Gly-Gln-Gly-Thr-Leu-Val-Thr-Val-Ser-Ala  240
```

Fig. 7

D x 3150H L scFv

```
  1 GAT GTA CAG CTT CAG GAG TCA GGA CCT GGC CTC GTG AAA CCT TCT CAG TCT CTG TCT CTC    60
    CTA CAT GTC GAA GTC CTC AGT CCT GGA CCG GAG CAC TTT GGA AGA GTC AGA GAC AGA GAG
  1 Asp-Val-Gln-Leu-Gln-Glu-Ser-Gly-Pro-Gly-Leu-Val-Lys-Pro-Ser-Gln-Ser-Leu-Ser-Leu    20
    VH→

61 ACC TGT TCT GTC ACT GGC TAC TCC ATC ACC AGT GGC TTT TAC TGG AAC TGG ATT CGG CAG   120
    TGG ACA AGA CAG TGA CCG ATG AGG TAG TGG TCA CCG AAA ATG ACC TTG ACC TAA GCC GTC
 21 Thr-Cys-Ser-Val-Thr-Gly-Tyr-Ser-Ile-Thr-Ser-Gly-Phe-Tyr-Trp-Asn-Trp-Ile-Arg-Gln    40

121 TTT CCA GGA AAC AAA CTG GAA TGG ATG GGC TAC ATA AGC TAC GAC GGT TAC AAT AAT TAC   180
    AAA GGT CCT TTG TTT GAC CTT ACC TAC CCG ATG TAT TCG ATG CTG CCA ATG TTA TTA ATG
 41 Phe-Pro-Gly-Asn-Lys-Leu-Glu-Trp-Met-Gly-Tyr-Ile-Ser-Tyr-Asp-Gly-Tyr-Asn-Asn-Tyr    60

181 AAC CCA TTT CTC AAA AAT CGA GTG TCC ATC ACT CGT GAC ACA TCT GAG AAC CAG TTT TTC   240
    TTG GGT AAA GAG TTT TTA GCT CAC AGG TAG TGA GCA CTG TGT AGA CTC TTG GTC AAA AAG
 61 Asn-Pro-Phe-Leu-Lys-Asn-Arg-Val-Ser-Ile-Thr-Arg-Asp-Thr-Ser-Glu-Asn-Gln-Phe-Phe    80

241 CTG AAG TTG CAT TCT GTG ACT ACT GAG GAC ACA GCT ACA TAT TAC TGT GTA AGT TAC GGT   300
    GAC TTC AAC GTA AGA CAC TGA TGA CTC CTG TGT CGA TGT ATA ATG ACA CAT TCA ATG CCA
 81 Leu-Lys-Leu-His-Ser-Val-Thr-Thr-Glu-Asp-Thr-Ala-Thr-Tyr-Tyr-Cys-Val-Ser-Tyr-Gly   100

301 AGT CGG AGG GGA GTT ACC TAC TGG GGC CAA GGT ACC ACT CTC ACA GTC TCC TCC GGA GGA   360
    TCA GCC TCC CCT CAA TGG ATG ACC CCG GTT CCA TGG TGA GAG TGT CAG AGG AGG CCT CCT
101 Ser-Arg-Arg-Gly-Val-Thr-Tyr-Trp-Gly-Gln-Gly-Thr-Thr-Leu-Thr-Val-Ser-Ser-          120

361 GGT GGT TCA GGC GGA GGT GGC TCT GGC GGT GGC GGA TCC CAG GCT GTT GTG ACT CAG GAA   420
    CCG CCA AGT CCG CCT CCA CCG AGA CCG CCA CCG CCT AGG GTC CGA CAA CAC TGA GTC CTT
121                                                                -Gln-Ala-Val-Val-Thr-Gln-Glu   140
                        Linker                                       VL→

421 TCT GCA CTC ACC ACA TCA CCT GGT GAA ACA GTC ACA CTC ACT TGT CGC TCA AGT ACT GGG   480
    AGA CGT GAG TGG TGT AGT GGA CCA CTT TGT CAG TGT GAG TGA ACA GCG AGT TCA TGA CCC
141 Ser-Ala-Leu-Thr-Thr-Ser-Pro-Gly-Glu-Thr-Val-Thr-Leu-Thr-Cys-Arg-Ser-Ser-Thr-Gly   160

481 GCT GTT ACA ACT AGT AAC TAT GCC AAC TGG GTC CAA GAA AAA CCA GAT CAT TTA TTC ACT   540
    CGA CAA TGT TGA TCA TTG ATA CGG TTG ACC CAG GTT CTT TTT GGT CTA GTA AAT AAG TGA
161 Ala-Val-Thr-Thr-Ser-Asn-Tyr-Ala-Asn-Trp-Val-Gln-Glu-Lys-Pro-Asp-His-Leu-Phe-Thr   180

541 GGT CTA ATA GGT AAT ACC AAC AAC CGA GCT CCA GGT GTT CCT GCC AGA TTC TCT GGC TCC   600
    CCA GAT TAT CCA TTA TGG TTG TTG GCT CGA GGT CCA CAA GGA CGG TCT AAG AGA CCG AGG
181 Gly-Leu-Ile-Gly-Asn-Thr-Asn-Asn-Arg-Ala-Pro-Gly-Val-Pro-Ala-Arg-Phe-Ser-Gly-Ser   200

601 CTG ATT GGA GAC AAG GCT GCC CTC ACC ATC ACA GGG GCA CAG ACT GAG GAT GAG GCG ATA   660
    GAC TAA CCT CTG TTC CGA CGG GAG TGG TAG TGT CCC CGT GTC TGA CTC CTA CTC CGC TAT
201 Leu-Ile-Gly-Asp-Lys-Ala-Ala-Leu-Thr-Ile-Thr-Gly-Ala-Gln-Thr-Glu-Asp-Glu-Ala-Ile   220

661 TAT TTC TGT GCT CTT TGG TAC AAC ACC CAT TTG GTG TTC GGT GGA GGA ACC AGA CTG ACT   720
    ATA AAG ACA CGA GAA ACC ATG TTG TGG GTA AAC CAC AAG CCA CCT CCT TGG TCT GAC TGA
221 Tyr-Phe-Cys-Ala-Leu-Trp-Tyr-Asn-Thr-His-Leu-Val-Phe-Gly-Gly-Gly-Thr-Arg-Leu-Thr   240

721 GTC CTA GGC   729
    CAG GAT CCG
241 Val-Leu-Gly   243
```

Fig. 8

Dx3150LH scFv

```
  1 CAG GCT GTT GTG ACT CAG GAA TCT GCA CTC ACC ACA TCA CCT GGT GAA ACA GTC ACA CTC   60
    GTC CGA CAA CAC TGA GTC CTT AGA CGT GAG TGG TGT AGT GGA CCA CTT TGT CAG TGT GAG
  1 Gln-Ala-Val-Val-Thr-Gln-Glu-Ser-Ala-Leu-Thr-Thr-Ser-Pro-Gly-Glu-Thr-Val-Thr-Leu   20
    VL→

61 ACT TGT CGC TCA AGT ACT GGG GCT GTT ACA ACT AGT AAC TAT GCC AAC TGG GTC CAA GAA  120
    TGA ACA GCG AGT TCA TGA CCC CGA CAA TGT TGA TCA TTG ATA CGG TTG ACC CAG GTT CTT
 21 Thr-Cys-Arg-Ser-Ser-Thr-Gly-Ala-Val-Thr-Thr-Ser-Asn-Tyr-Ala-Asn-Trp-Val-Gln-Glu   40

121 AAA CCA GAT CAT TTA TTC ACT GGT CTA ATA GGT AAT ACC AAC AAC CGA GCT CCA GGT GTT  180
    TTT GGT CTA GTA AAT AAG TGA CCA GAT TAT CCA TTA TGG TTG TTG GCT CGA GGT CCA CAA
 41 Lys-Pro-Asp-His-Leu-Phe-Thr-Gly-Leu-Ile-Gly-Asn-Thr-Asn-Asn-Arg-Ala-Pro-Gly-Val   60

181 CCT GCC AGA TTC TCT GGC TCC CTG ATT GGA GAC AAG GCT GCC CTC ACC ATC ACA GGG GCA  240
    GGA CGG TCT AAG AGA CCG AGG GAC TAA CCT CTG TTC CGA CGG GAG TGG TAG TGT CCC CGT
 61 Pro-Ala-Arg-Phe-Ser-Gly-Ser-Leu-Ile-Gly-Asp-Lys-Ala-Ala-Leu-Thr-Ile-Thr-Gly-Ala   80

241 CAG ACT GAG GAT GAG GCG ATA TAT TTC TGT GCT CTT TGG TAC AAC ACC CAT TTG GTG TTC  300
    GTC TGA CTC CTA CTC CGC TAT ATA AAG ACA CGA GAA ACC ATG TTG TGG GTA AAC CAC AAG
 81 Gln-Thr-Glu-Asp-Glu-Ala-Ile-Tyr-Phe-Cys-Ala-Leu-Trp-Tyr-Asn-Thr-His-Leu-Val-Phe  100

301 GGT GGA GGA ACC AGA CTG ACT GTC CTA GGC TCC GGA GGA GGC GGT TCA GGC GGA GGT GGC  360
    CCA CCT CCT TGG TCT GAC TGA CAG GAT CCG AGG CCT CCT CCG CCA AGT CCG CCT CCA CCG
101 Gly-Gly-Gly-Thr-Arg-Leu-Thr-Val-Leu-Gly-Ser-Gly-Gly-Gly-Gly-Ser-Gly-Gly-Gly-Gly  120
                                                         Linker 361 TCT GGC GGT GGC GGA TCC GAT GTA CAG CTT CAG GAG TCA GGA CCT GGC CTC GTG AAA CCT  420
    AGA CCG CCA CCG CCT AGG CTA CAT GTC GAA GTC CTC AGT CCT GGA CCG GAG CAC TTT GGA
121 Ser-Gly-Gly-Gly-Gly-Ser-Asp-Val-Gln-Leu-Gln-Glu-Ser-Gly-Pro-Gly-Leu-Val-Lys-Pro  140
                      VH→

421 TCT CAG TCT CTG TCT CTC ACC TGT TCT GTC ACT GGC TAC TCC ATC ACC AGT GGC TTT TAC  480
    AGA GTC AGA GAC AGA GAG TGG ACA AGA CAG TGA CCG ATG AGG TAG TGG TCA CCG AAA ATG
141 Ser-Gln-Ser-Leu-Ser-Leu-Thr-Cys-Ser-Val-Thr-Gly-Tyr-Ser-Ile-Thr-Ser-Gly-Phe-Tyr  160

481 TGG AAC TGG ATT CGG CAG TTT CCA GGA AAC AAA CTG GAA TGG ATG GGC TAC ATA AGC TAC  540
    ACC TTG ACC TAA GCC GTC AAA GGT CCT TTG TTT GAC CTT ACC TAC CCG ATG TAT TCG ATG
161 Trp-Asn-Trp-Ile-Arg-Gln-Phe-Pro-Gly-Asn-Lys-Leu-Glu-Trp-Met-Gly-Tyr-Ile-Ser-Tyr  180

541 GAC GGT TAC AAT AAT TAC AAC CCA TTT CTC AAA AAT CGA GTG TCC ATC ACT CGT GAC ACA  600
    CTG CCA ATG TTA TTA ATG TTG GGT AAA GAG TTT TTA GCT CAC AGG TAG TGA GCA CTG TGT
181 Asp-Gly-Tyr-Asn-Asn-Tyr-Asn-Pro-Phe-Leu-Lys-Asn-Arg-Val-Ser-Ile-Thr-Arg-Asp-Thr  200

601 TCT GAG AAC CAG TTT TTC CTG AAG TTG CAT TCT GTG ACT ACT GAG GAC ACA GCT ACA TAT  660
    AGA CTC TTG GTC AAA AAG GAC TTC AAC GTA AGA CAC TGA TGA CTC CTG TGT CGA TGT ATA
201 Ser-Glu-Asn-Gln-Phe-Phe-Leu-Lys-Leu-His-Ser-Val-Thr-Thr-Glu-Asp-Thr-Ala-Thr-Tyr  220

661 TAC TGT GTA AGT TAC GGT AGT CGG AGG GGA GTT ACC TAC TGG GGC CAA GGC ACC ACT CTC  720
    ATG ACA CAT TCA ATG CCA TCA GCC TCC CCT CAA TGG ATG ACC CCG GTT CCG TGG TGA GAG
221 Tyr-Cys-Val-Ser-Tyr-Gly-Ser-Arg-Arg-Gly-Val-Thr-Tyr-Trp-Gly-Gln-Gly-Thr-Thr-Leu  240

721 ACA GTC TCC TCA  732
    TGT CAG AGG AGT
241 Thr-Val-Ser-Ser  244
```

```
                                                 CDR1
               10           20           30            40
WT      EVKLVESGGGLVKPGGSLKLSCAAS G F T F S S Y AMSWVRQT
HL-M#5  ------------------------ - - - - - - - -------
LH-M#1  ----------R------------- - - - - - - - -------
LH-M#2  ------------------------ - - - - - - - -------
LH-M#3  ------------------------ - - - - - - - -------

CDR2
             50           60           70            80
WT      PEKRLEWVAS F S NGG I TYYPDSVKGRFTISRDNARNILYL
HL-M#5  ---------- I -------- ---------------------
LH-M#1  ---------- L -------- ---------------------
LH-M#2  ---------- V -------- ---------------------
LH-M#3  ---------- L -------- ------------------V---

CDR3
             90          100          110    114
WT      QMTSLRSEDTAIYYC A R G Y G P A Y WGQGTLVTVSA
HL-M#5  -------------- - - - - - - - - ---------S
LH-M#1  -------------- - - - - - - - - ---------A
LH-M#2  -------------- - - - - - - - - --H------A
LH-M#3  -------------- - - - - - - - - ---------A
```

Fig. 13
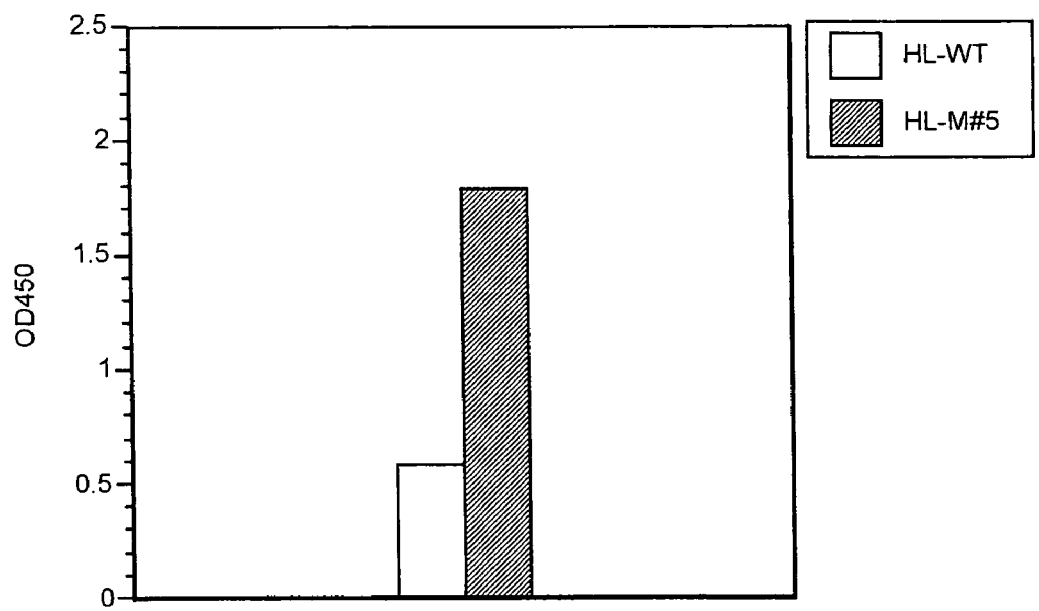
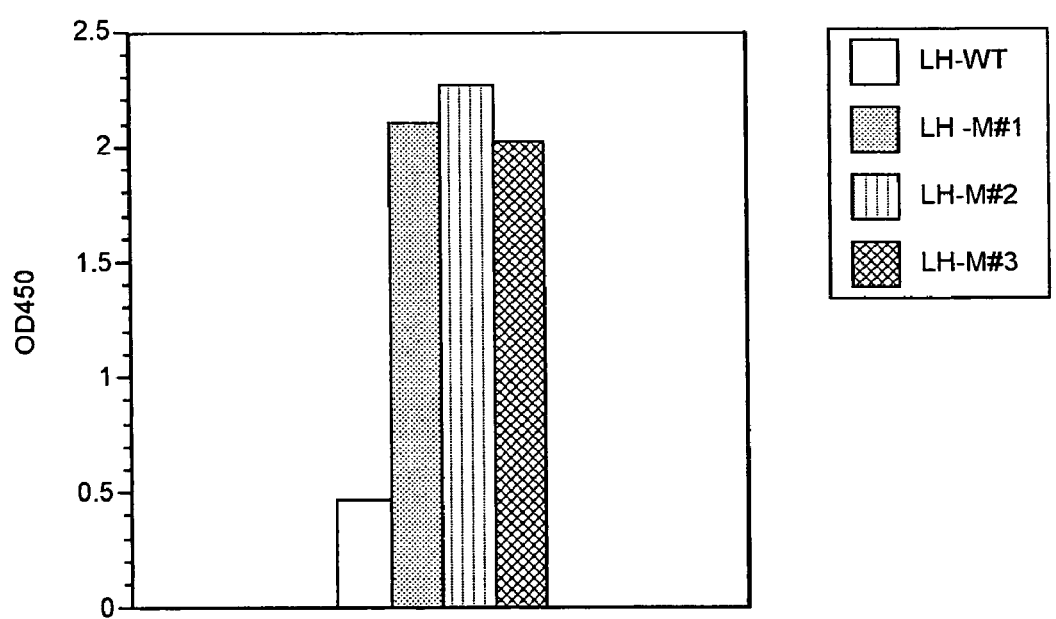

Fig. 14
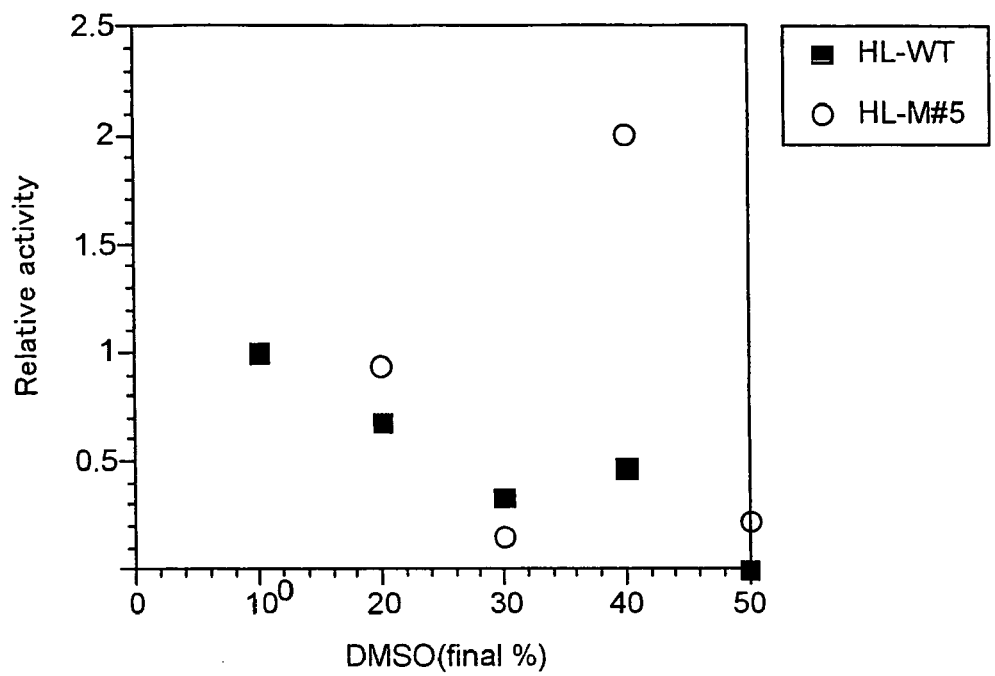
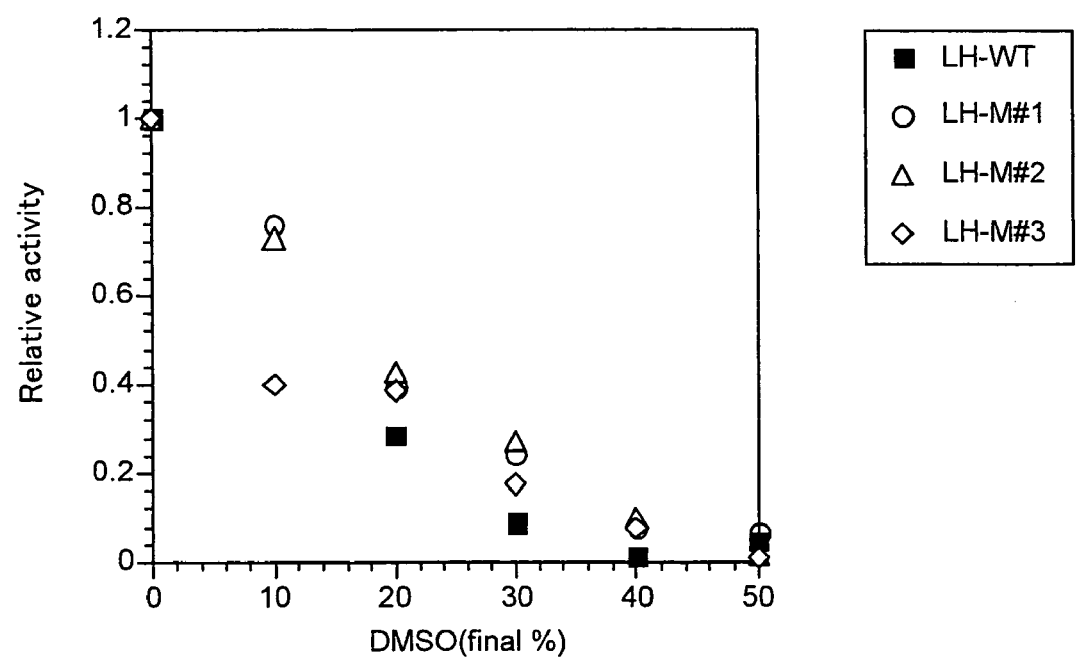

RECOMBINANT ANTIBODY RECOGNIZING DIOXIN AND GENE ENCODING THE ANTIBODY

TECHNICAL FIELD

The present invention relates to a novel recombinant antibody having a binding activity to 2,3,4,7,8-pentachlorodibenzofuran (2,3,4,7,8-PeCDF), a gene encoding its amino acid sequence, a vector incorporating said gene, a transformant transformed with said vector, a process for preparing said recombinant antibody, and methods for immunologically capturing and determining 2,3,4,7,8-PeCDF using said recombinant antibody.

BACKGROUND ART

The environmental pollution by endocrine disruptors becomes problems, and research of the state of pollution, investigation of the influence on the health of human beings and the like have been carried out. As the influences of these endocrine disruptors on human beings and on the environment are revealed, they became great social concerns not only in Japan but also in many countries of the world. Among others, dioxins are suspected of lasting influences on human beings and on the ecosystem and environment, and therefore, research of the state of pollution, investigation of the state of exposure in human beings and in the ecosystem and elucidation of intake routes as well as development of a method of monitoring the amount of dioxins in polluted locations and a method of removing the pollution are accelerated. Since dioxins are formed, for example, in the course of use, production and combustion of organic chlorine compounds, the sources of the dioxins are wide-ranging and a widespread pollution is confirmed in soil, water, atmosphere, foods, marine products and the like. Accordingly, it is desired to establish a simple and rapid method for determining dioxins in samples, owing to the need of determining dioxin concentrations in numerous samples such as biological and environmental samples, and of taking measures to the pollution.

Dioxins include a number of congeners comprised of 75 kinds of polychlorodibenzodioxins (PCDDs) and 135 kinds of polychlorodibenzofurans (PCDFs). The relative toxicity of each dioxin congener, when assuming that the toxicity of 2,3,7,8-tetrachlorodibenzo-p-dioxin (2,3,7,8-TCDD) having the highest toxicity is 1, is shown as Toxic Equivalency Factor, and 7 kinds of PCDDs and 10 kinds of PCDFs having a high toxicity are used as object substances for measurement in the analysis of dioxins. Also, of polychlorobiphenyls (PCBs) which are recognized as one group of endocrine disruptors and are seen as a problem for some time, 12 kinds of co-planar PCBs have been measured as dioxins.

Previously, the determination of dioxins has been carried out by means of a high-resolution gas chromatography/mass spectrometry (HRGC/HRMS) analysis. However, the HRGC/HRMS method needs a multi-stage of complicated cleanup procedures to remove interfering substances contained in samples, an expensive analytical instrument, and skilled analyzers. Accordingly, the use of the method is limited to an analysis in a particular analytical facility. In analytical methods of dioxins, in particular, in the RGC/HRMS method, the contents of 17 kinds of dioxin congeners each having a high toxicity value are individually quantified, and the actually quantified content of each congener is then multiplied by the corresponding Toxic Equivalency Factor. Then, the sum total of the values obtained for all the congeners is calculated as Toxic Equivalent Quantity (TEQ) which corresponds to the amount of 2,3,7,8-TCDD, and the TEQ values are used as analytical values of the dioxins. Thus, the method needs much time for analysis of samples involving data analysis. For the above reasons, it is strongly desired to develop a convenient, cheep and highly sensitive method for determining dioxins in samples.

On the other hand, there persistently exists an idea that the dioxin amount (TEQ) is more simply determined by measuring a particular indicator substance. One of these methods is that measuring chlorobenzene which is a precursor of dioxins. Recently, it has been proved that the amount of 2,3,4,7,8-PeCDF, which is one of dioxin congeners, has a very high correlation with the total TEQ value of dioxins (Takasuga et al., 11th Symposium on Environmental Chemistry, Program and Abstracts, p. 136, 2002). In a wide range of samples, for example, environmental samples such as soil, mud, atmosphere, water, exhaust gas and ash, biological samples such as mother's milk and blood as well as marine products, foods and the like, 2,3,4,7,8-PeCDF is a major constituent in all dioxins, and its content shows a high correlation (R=0.96-0.99) with the total TEQ value of dioxins. Accordingly, attention is paid to 2,3,4,7,8-PeCDF as an indicator substance for investigating the amount of dioxins.

On the other hand, an attempt to quantify the dioxins using an antibody is also made in the art.

For example, JP-A-2002/340882 discloses a method for determining dioxins and an apparatus therefor comprising four units, i.e. a collection unit, an extraction unit, a separation and purification unit, and a measurement unit for determining dioxins using an antibody.

Also, JP-A-2002/228660 discloses a method for detecting dioxins contained in biological samples such as human blood and mother's milk by preparing and using a monoclonal antibody having a high affinity for 2,3,7,8-TCDD.

In addition, JP-A-2002/119279 discloses a method for deducing an amount of dioxins present in samples using a few antibodies having a cross-reactivity with plural congeners within the range of dioxin.

However, these references do not disclose monoclonal antibodies recognizing 2,3,4,7,8-PeCDF, as well as, gene sequences encoding said monoclonal antibodies, recombinant antibodies based on said gene sequences and a method for determining 2,3,4,7,8-PeCDF using said recombinant antibodies.

Also, methods disclosed in these references have a disadvantage that they are insufficient for investigating the TEQ values of dioxins contained in samples.

DISCLOSURE OF THE INVENTION (Technical Problem to be Solved by the Invention)

The present inventors intended to establish a rapid, convenient and highly sensitive method for capturing and determining an indicator substance, 2,3,4,7,8-PeCDF by an immunological technique, the indicator substance being a major constituent among 17 kinds of dioxins determined by the HRGC/HRMS method, and the content of the indicator substance having a high correlation with the total TEQ value of dioxins.

(Means of Solving the Problem)

In order to solve the above problem, the present inventors prepared two hybridomas producing monoclonal antibodies recognizing 2,3,4,7,8-PeCDF, i.e. hybridoma Dx3860r1 producing monoclonal antibody Dx3860 and hybridoma Dx3150r1 producing monoclonal antibody Dx3150, by a conventional cell fusion method using a 2,3,4,7,8-PeCDF derivative as an antigen.

Then, the present inventors isolated and purified mRNAs contained in these hybridomas, and synthesized cDNAs on the basis of the mRNAs. Subsequently, in order to select cDNAs encoding the heavy chain (H-chain) variable region and light chain (L-chain) variable region of monoclonal antibody Dx3860 as well as the H-chain variable region and L-chain variable region of monoclonal antibody Dx3150 from the synthesized cDNAs, PCR was carried out using antibody gene-specific sequences and the desired antibody genes were specifically amplified. The base sequences of the cDNAs selected were analyzed, and the amino acid sequences encoded by them were deduced.

As a result, it was found that cDNAs encoding the H-chain variable region and L-chain variable region of monoclonal antibody Dx3860 are shown by SEQ ID Nos. 1 and 2, respectively, and cDNAs encoding the H-chain variable region and L-chain variable region of monoclonal antibody Dx3150 are shown by SEQ ID Nos. 3 and 4, respectively.

Also, it was found that deduced amino acid sequences of the H-chain variable region and L-chain variable region of monoclonal antibody Dx3860 are shown by SEQ ID Nos. 5 and 6, respectively, and deduced amino acid sequences of the H-chain variable region and L-chain variable region of monoclonal antibody Dx3150 are shown by SEQ ID Nos. 7 and 8, respectively.

In addition, the present inventors specified the amino acid sequences and positions of hypervariable domains (CDRs 1-3) in the variable regions of the above antibodies. The amino acid sequences of the hypervariable domains are shown in the following Tables 1-4.

TABLE 1

Amino acid sequences of the hypervariable domains in the H-chain variable region of Dx3860

| | | |
|---|---|---|
| CDR 1 | Gly-Phe-Thr-Phe-Ser-Ser-Tyr-Ala | SEQ ID No. 9 |
| CDR 2 | Phe-Ser-Asn-Gly-Gly-Ile-Thr | SEQ ID No. 10 |
| CDR 3 | Ala-Arg-Gly-Tyr-Gly-Pro-Ala-Tyr | SEQ ID No. 11 |

TABLE 2

Amino acid sequences of the hypervariable domains in the L-chain variable region of Dx3860

| | | |
|---|---|---|
| CDR 1 | Thr-Gly-Ala-Val-Thr-Thr-Leu-Asn-Tyr | SEQ ID No. 12 |
| CDR 2 | Asn-Thr-Asn | |
| CDR 3 | Ala-Leu-Trp-Tyr-Ser-Asn-His-Leu | SEQ ID No. 13 |

TABLE 3

Amino acid sequences of the hypervariable domains in the H-chain variable region of Dx3150

| | | |
|---|---|---|
| CDR 1 | Gly-Tyr-Ser-Ile-Thr-Ser-Gly-Phe-Tyr | SEQ ID No. 14 |
| CDR 2 | Ile-Ser-Tyr-Asp-Gly-Tyr-Asn | SEQ ID No. 15 |

TABLE 3-continued

Amino acid sequences of the hypervariable domains in the H-chain variable region of Dx3150

| | | |
|---|---|---|
| CDR 3 | Val-Ser-Tyr-Gly-Ser-Arg-Arg-Gly-Val-Thr-Tyr | SEQ ID No. 16 |

TABLE 4

Amino acid sequences of the hypervariable domains in the L-chain variable region of Dx3150

| | | |
|---|---|---|
| CDR 1 | Thr-Gly-Ala-Val-Thr-Thr-Ser-Asn-Tyr | SEQ ID No. 17 |
| CDR 2 | Asn-Thr-Asn | |
| CDR 3 | Ala-Leu-Trp-Tyr-Asn-Thr-His-Leu-Val | SEQ ID No. 18 |

The positions of the hypervariable domains (CDRs 1-3) in the H-chain and L-chain variable regions of monoclonal antibody Dx3860 are shown in FIG. 1 and FIG. 2, respectively, together with the DNA sequences and amino acid sequences. Also, the positions of the hypervariable domains (CDRs 1-3) in the H-chain and L-chain variable regions of monoclonal antibody Dx3150 are shown in FIG. 3 and FIG. 4, respectively, together with the DNA sequences and amino acid sequences.

In FIG. 1, positions 26-33 of the amino acid sequence represent CDR1; positions 51-57 CDR2; and positions 96-103 CDR3.

In FIG. 2, positions 26-34 of the amino acid sequence represent CDR1; positions 52-54 CDR2; and positions 91-98 CDR3.

In FIG. 3, positions 26-34 of the amino acid sequence represent CDR1; positions 52-58 CDR2; and positions 97-107 CDR3.

In FIG. 4, positions 26-34 of the amino acid sequence represent CDR1; positions 52-54 CDR2; and positions 91-99 CDR3.

Also, the present inventors integrated DNAs encoding the variable regions of the above antibodies into an expression vector, introduced the resultant vectors into host cells, and expressed recombinant antibodies in said host cells. Moreover, the present inventors confirmed that 2,3,4,7,8-PeCDF in samples can be quantified by using said recombinant antibodies. Furthermore, the present inventors introduced a mutation into DNAs encoding the variable regions of the above antibodies, expressed recombinant antibodies as described above by using the resultant mutation-introduced DNAs, and confirmed that 2,3,4,7,8-PeCDF in samples can be quantified by using said recombinant antibodies.

Accordingly, the present invention relates to a recombinant antibody having a binding activity to 2,3,4,7,8-pentachlorodibenzofuran (2,3,4,7,8-PeCDF), which comprises at least one polypeptide selected from the group consisting of:

(1) a polypeptide constituting the H-chain variable region of monoclonal antibody Dx3860 recognizing 2,3,4,7,8-PeCDF, and having the amino acid sequence as shown in SEQ ID No. 5;

(2) a polypeptide constituting the L-chain variable region of said monoclonal antibody Dx3860, and having the amino acid sequence as shown in SEQ ID No. 6;

(3) a polypeptide constituting the H-chain variable region of monoclonal antibody Dx3150 recognizing 2,3,4,7,8-PeCDF, and having the amino acid sequence as shown in SEQ ID No. 7;

(4) a polypeptide constituting the L-chain variable region of said monoclonal antibody Dx3150, and having the amino acid sequence as shown in SEQ ID No. 8;

(5) polypeptides having amino acid sequences showing not less than 95% of homology to the amino acid sequences of the above polypeptides (1)-(4), and having a binding activity to 2,3,4,7,8-PeCDF; and (6) polypeptides representing fragments of the above polypeptides (1)-(5), and having a binding activity to 2,3,4,7,8-PeCDF.

The present invention also relates to a DNA encoding the amino acid sequence of the above recombinant antibody, a cloning or expression vector comprising said DNA, a transformant transformed with said vector, a method for preparing said recombinant antibody using said transformant as well as methods for immunologically capturing and determining 2,3,4,7,8-PeCDF using said recombinant antibody.

(Advantageous Effects Over the Prior Art)

It is possible to capture and determine dioxins, particularly 2,3,4,7,8-PeCDF, in a rapid, convenient and highly sensitive manner by an immunological technique using the recombinant antibody according to the present invention.

BRIEF DESCRIPTION OF DRAWINGS

FIG. 1 shows the DNA sequence, amino acid sequence and positions of the hypervariable domains (CDRs 1-3) of the H-chain variable region of monoclonal antibody Dx3860.

FIG. 2 shows the DNA sequence, amino acid sequence and positions of the hypervariable domains (CDRs 1-3) of the L-chain variable region of monoclonal antibody Dx3860.

FIG. 3 shows the DNA sequence, amino acid sequence and positions of the hypervariable domains (CDRs 1-3) of the H-chain variable region of monoclonal antibody Dx3150.

FIG. 4 shows the DNA sequence, amino acid sequence and positions of the hypervariable domains (CDRs 1-3) of the L-chain variable region of monoclonal antibody Dx3150.

FIG. 5 shows the constitution of scFv fragment Dx3860HL.

FIG. 6 shows the constitution of scFv fragment Dx3860LH.

FIG. 7 shows the constitution of scFv fragment Dx3150HL.

FIG. 8 shows the constitution of scFv fragment Dx3150LH.

FIG. 13 represents a graph comparing the antibody titers of mutation-introduced Dx3860 scFv-displaying phages.

FIG. 14 represents a graph of comparing the reactivity of mutation-introduced Dx3860 scFv-displaying phages in the presence of DMSO.

BEST MODE FOR PRACTICING THE INVENTION

Figure 9:
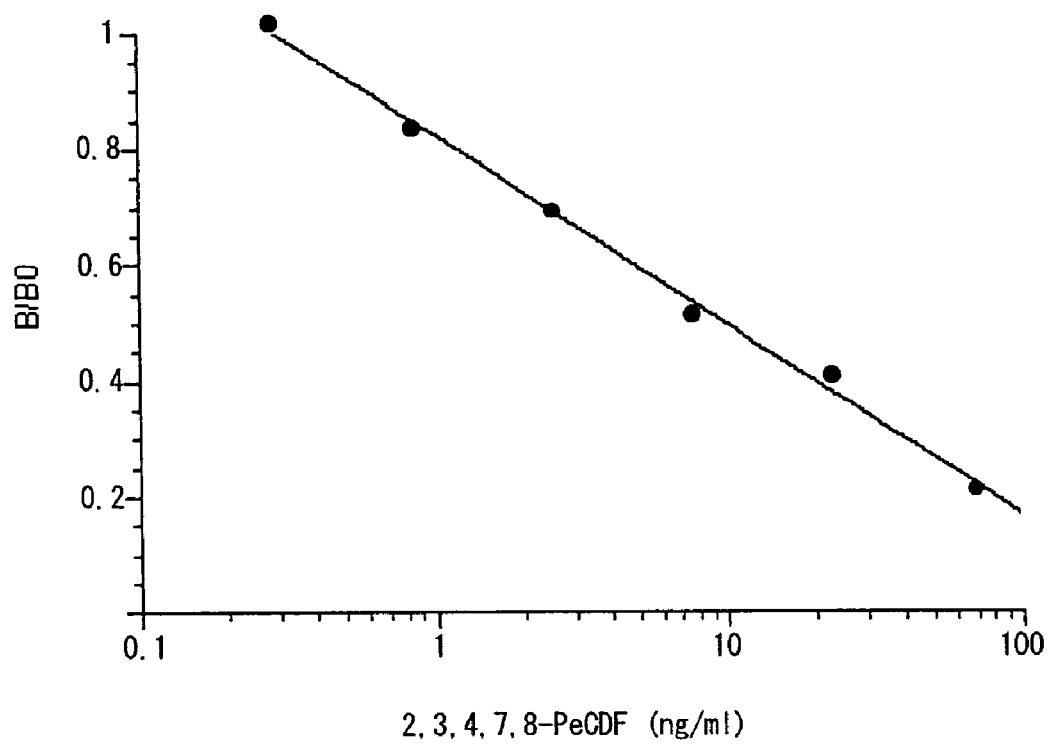
FIG. 9 represents a graph showing the results of determining 2,3,4,7,8-PeCDF by an indirect competitive immunoassay using an anti-2,3,4,7,8-PeCDF scFv.

In the context of the present invention, the term "antibody" includes, in addition to naturally-occurring antibodies present in the living body, polypeptides which are formed by the H-chain or L-chain variable region of an antibody or by a combination thereof and have at least one antigen-binding site. Such polypeptides include, for example, polypeptides containing only the H-chain or L-chain variable region, Fab fragments containing one set of the H-chain fragment and L-chain, F(ab')$_2$ fragments containing two sets of the H-chain fragments and L-chains, and single-chain recombinant antibodies (scFvs) in which the H-chain variable region and L-chain variable region are linked via a linker to form a single-chain.

For example, scFvs include polypeptides containing "(H-chain variable region)-(linker)-(L-chain variable region)" in this order starting from the N-terminal side as well as polypeptides containing "(L-chain variable region)-(linker)-(H-chain variable region)" in this order starting from the N-terminal side. The linker is positioned between these regions so that the H-chain variable region and L-chain variable region are efficiently folded when the scFv binds to an antigen. The linker usually consists of 5 to 15 amino acids, and includes -(Gly$_4$Ser)$_3$-, for example. The linker used in the present invention is not limited by the number and type of amino acids so far as the above purpose is achieved.

Also, in the recombinant antibodies according to the present invention, further suitable amino acid sequences may be added to the N-terminal side and C-terminal side of the H-chain variable region or L-chain variable region. For example, in the case of "(H-chain variable region)-(linker)-(L-chain variable region)" polypeptides, it is possible to add a secretory signal sequence to the N-terminal side of the H-chain variable region and an epitope tag sequence to the C-terminal side of the L-chain variable region, as shown in the Examples below. Also, in the case of "(L-chain variable region)-(linker)-(H-chain variable region)" polypeptides, it is possible to add a secretory signal sequence to the N-terminal side of the L-chain variable region and an epitope tag sequence to the C-terminal side of the H-chain variable region.

The recombinant antibodies according to the present invention include, in addition to polypeptides having at least one antigen-binding site which are formed by the H-chain or L-chain variable region of an antibody or a combination of these regions, mutated polypeptides having substantially the same functions as those of the former polypeptides. In the context of the present invention, the term "substantially the same function" means that the binding force to an antigen is substantially identical. Thus, the H-chain and L-chain variable regions of the present anti-2,3,4,7,8-PeCDF antibodies, which have the amino acid sequences as shown in SEQ ID Nos. 5-8, can contain deletion, substitution or addition mutations of one or more amino acids so far as the binding force to an antigen is substantially identical. Such a mutated polypeptide according to the present invention has preferably not less than 95%, more preferably not less than 98%, and most preferably not less than 99% of homology to the amino acid sequences as shown in SEQ ID Nos. 5-8. Also, the mutation is preferably present in a framework other than the hypervariable domains (CDRs 1-3) in antibody variable regions as shown in FIGS. 1-4.

Furthermore, the recombinant antibodies according to the present invention include fragments of the polypeptides as shown in SEQ ID Nos. 5-8 which have substantially the same functions as those of the original polypeptides, and polypeptides formed by a combination of these fragments. These fragments contain at least one, preferably two and more preferably all three of the hypervariable domains (CDRs 1-3) as shown in FIGS. 1-4.

The recombinant antibody according to the present invention can be produced by preparing a DNA encoding an amino acid sequence of a desired polypeptide, integrating said DNA into an expression vector, introducing said expression vector into host cells, and cultivating said host cells in a suitable medium to express said recombinant antibody.

The DNA encoding an amino acid sequence of a desired polypeptide can be prepared by synthesis on the basis of the cDNA sequences or amino acid sequences as shown in SEQ ID Nos. 1-4 (or FIGS. 1-4). Alternatively, the DNA encoding an amino acid sequence of a desired polypeptide can be obtained as follows. Thus, as shown in the Examples below, the present inventors constructed an expression vector which integrates a fragment containing the H-chain variable region of monoclonal antibody Dx3860, a linker, and the L-chain variable region of Dx3860 in this order starting from the N-terminal side (see FIG. 5), introduced the vector into Escherichia coli B, and deposited the resultant E. coli B (pET22Δ-Dx3860HL) to International Patent Organism Depositary. Also, the present inventors constructed an expression vector which integrates a fragment containing the H-chain variable region of monoclonal antibody Dx3150, a linker, and the L-chain variable region of Dx3150 in this order starting from the N-terminal side (see FIG. 7), introduced the vector into Escherichia coli K-12, and deposited the resultant E. coli K-12 (pET22Δ-Dx3150HL) to International Patent Organism Depositary. The DNA encoding an amino acid sequence of a desired polypeptide can be obtained by cleaving from these expression vectors using a suitable restriction enzyme, and optionally by introducing mutation into the resultant DNA sequence. For the purpose of ligation of DNA fragments, of course, it is possible to modify the termini of the fragments by a conventional method.

The integration of the resultant DNA fragment into an expression vector can be carried out by tailoring the termini of the DNA fragment so as to adapt to a given fragment-insertion site of a commercially available expression vector [for example, pET-22b(+)], and inserting the terminus-tailored DNA fragment into the expression vector.

The expression vector thus obtained can be introduced into suitable host cells, particularly Escherichia coli [for example, E. coli B strain, K-12 strain, BL21(DE3) strain, etc.], and the host cells can be cultivated in a medium suitable for expression of the inserted DNA fragment to express the desired recombinant antibody. The recombinant antibody expressed can be recovered from the host cells or a culture thereof by a conventional method. The recombinant antibody recovered can be purified, for example, by a chromatography method.

Using the above process, it is possible to prepare the desired recombinant antibody at low cost and in a large amount, as compared with a monoclonal antibody obtained by cultivating animal cells in a medium in need of serum.

Using the resultant recombinant antibody, it is possible to immunologically capture 2,3,4,7,8-PeCDF in samples rapidly. Such a capturing method includes separation, purification and concentration methods of 2,3,4,7,8-PeCDF by immuno-chromatography or immuno-precipitation. Also, using the recombinant antibody and using the above action of capturing 2,3,4,7,8-PeCDF, it is possible to rapidly capture and remove 2,3,4,7,8-PeCDF which is a main substance of dioxins taken in the living body.

Moreover, using the resultant recombinant antibody, it is possible to immunologically determine 2,3,4,7,8-PeCDF in samples in a rapid and highly sensitive manner. Such a determining method includes radioimmunoassay (RIA), enzyme immunoassay (EIA), fluoroimmunoassay (FIA) and the like.

The immunologically determining methods are classified broadly into non-competitive methods and competitive methods. The recombinant antibodies according to the present invention are preferably used for competitive methods. The competitive methods include indirect competitive methods and direct competitive methods. In the indirect competitive methods, a 2,3,4,7,8-PeCDF derivative is immobilized, and the reaction with the recombinant antibody is allowed to compete between free 2,3,4,7,8-PeCDF in samples and the immobilized antigen. In the direct competitive methods, the recombinant antibody is immobilized, and the amount of a labeled 2,3,4,7,8-PeCDF derivative is determined which binds to the immobilized recombinant antibody depending on the amount of 2,3,4,7,8-PeCDF present in samples.

EXAMPLES

The present invention is illustrated in more detail based on the following examples, but it is not limited thereto.

Preparation of Hybridomas Producing an Anti-2,3,4,7,8-PeCDF Antibody

Hybridomas producing a monoclonal antibody recognizing 2,3,4,7,8-PeCDF were prepared as follows. Thus, an alkyl chain was firstly introduced into 2,3,4,7,8-PeCDF and the terminus of the alkyl chain was converted into an active ester. The product was then introduced into bovine serum albumin (BSA) as a carrier protein according to a conventional method to prepare a conjugate for immunization.

The conjugate for immunization was thoroughly emulsified in an adjuvant RAS R-700 (Ribi Co.). The emulsion (200 μl) was administered into the peritoneal cavity of BALB/c mice (7 weeks age, male) to immunize the mice. Booster immunizations were carried out at intervals of two weeks, blood samples were taken from the tail vein after the passage of about one week from each booster immunization, and the antibody titer in blood was determined by a competitive EIA method.

Mice in which a high level production of an antibody against 2,3,4,7,8-PeCDF was confirmed were selected and the conjugate for immunization was administered into the tail vein of the mice to carry out final immunization. After 3 to 4 days from the final immunization, the spleen was removed from the mice and spleen cells were prepared. Mouse myeloma cells (Sp2/O) in a logarithmic growth phase and the spleen cells were mixed in a ratio of 1:5, and cell fusion was carried out by a polyethylene glycol method (PEG method). The cells after fusion were suspended in a HAT medium containing 10% FCS. The suspension was pipetted into a 96-well culturing plate ($1\text{-}2.5\times10^5$/well), and cultivated at 37° C. under 5% $CO_2$.

After 7 to 10 days from the onset of the cultivation, a portion of the supernatant of the culture in the wells in which proliferation of hybridomas was observed was taken and added to a microtiter plate to which the 2,3,4,7,8-PeCDF derivative-BSA conjugate was immobilized. After allowing to react at room temperature for one hour, the plate was washed with PBS(−) containing 0.05% Tween 20. A peroxidase-labeled anti-mouse IgG antibody (recognizing γ-chain) (KPL Co.) was then added to the plate and allowed to react at room temperature for one hour, and the plate was then washed in the same manner. A substrate solution (TMB substrate, KPL Co.) was added to the plate, the peroxidase activity on the plate was measured, and the antibody titer in the supernatant of the culture was determined. Of the wells showing a high antibody titer, the wells in which the antibody titer to the immobilized 2,3,4,7,8-PeCDF derivative-BSA conjugate was largely inhibited by 2,3,4,7,8-PeCDF dissolved in 20% DMSO were selected, and the hybridomas in the wells were cloned by a limiting dilution method. Two clones producing the monoclonal antibody recognizing 2,3,4,7,8-PeCDF were established by cultivating the cells isolated by the above cloning.

Thus, hybridoma Dx3860r1 producing monoclonal antibody Dx3860 and hybridoma Dx3150r1 producing monoclonal antibody Dx3150 were obtained as described above.

Isolation and Purification of mRNA

Hybridomas Dx3860r1 and Dx3150r1 producing anti-2,3,4,7,8-PeCDF antibody were grown in a RPMI 1640 medium containing 10% FCS under a 5% $CO_2$ aeration condition. From about $2.8-5.0 \times 10^7$ cells in a logarithmic growth phase, all RNAs were extracted by a AGPC method [Chomczynski, P., Sacchi, N., Anal. Biochem., 162, p. 156-159 (1987)]. Then, poly(A) +RNA was purified using Origotex-dT 30 (latex beads to which oligo dT is bound; Takara Shuzo Co.).

Synthesis of cDNA

Using Primed first-strand reaction mix contained in Mouse scFv Module/Recombinant Phage Antibody System (Amersham Pharmacia Co.), cDNA was synthesized from the above poly(A) +RNA. The PCR was carried out using the resultant cDNA as a template and using Mouse Ig-Primer Set (Novagen) and Taq DNA polymerase (Applied Biosystems Co.). The primer set of MuIgV$_H$5'-A and MuIgV$_H$3'-2 was used for Dx3860 H-chain, and the primer set of MuIgV$_H$5'-D and MuIgV$_H$3'-2 for Dx3150 H-chain. Also, the primer set of MuIgλV$_L$5'-A and MuIgλV$_L$3'-1 was used for both Dx3860 L-chain and Dx3150 L-chain. The primers used are shown in Table 5 below. The PCR reaction was carried out as follows. Thus, the reaction cycle of 94° C.×1 minute, 50° C.×1 minute and 72° C.×1 minute was repeated 30 cycles for Dx3860 H-chain and Dx3150 L-chain; the reaction cycle of 94° C.×1 minute, 60° C.×1 minute and 72° C.×1 minute 30 cycles for Dx3150 H-chain; and the reaction cycle of 94° C.×1 minute, 60° C.×1 minute and 72° C.×1 minute 5 cycles and then the reaction cycle of 94° C.×1 minute, 50° C.×1 minute and 72° C.×1 minute 30 cycles for Dx3860 L-chain.

TABLE 5

PCR primers for synthesis of cDNAs

H-chain 5'-side

```
Dx3860 MuIgV_H5'-A   GGGAATTCATGRASTTSKGGYTMARCTKGRTTT   (SEQ ID No. 19)
Dx3150 MuIgV_H5'-D   ACTAGTCGACATGGRCAGRCTTACWTYYTCATTCCT (SEQ ID No. 20)
                     ACTAGTCGACATGATGGTGTTAAGTCTTCTGTACCT (SEQ ID No. 21)
                     ACTAGTCGACATGGGATGGAGCTRTATCATSYTCTT (SEQ ID No. 22)
```

H-chain 3'-side (for Dx3860 and Dx3150 in common)

```
       MuIgV_H3'-2   CCCAAGCTTCCAGGGRCCARKGGATARACIGRTGG  (SEQ ID No. 23)
```

L-chain 5'-side (for Dx3860 and Dx3150 in common)

```
       MUIgλV_L5'-A  GGGAATTCATGGCCTGGAYTYCWCTYWTMYTCT    (SEQ ID No. 24)
```

L-chain 3'-side (for Dx3860 and Dx3150 in common)

```
       MuIgλV_L3'-1  CCCAAGCTTAGCTCYTCWGWGGAIGGYGGRAA     (SEQ ID No. 25)
```

Subcloning of cDNA

The above PCR products were inserted into pGEM-T Easy using a TA cloning kit: pGEM-T Easy Vector System I (Promega Co.), and *Escherichia coli* XL1-Blue was then transformed using the inserts. XL1-Blue Competent Cells (STRATAGENE Co.) were used as competent cells.

Determination of Base Sequences and Analysis of Amino Acid Sequences

For antibody gene cDNA clones subcloned into pGEM-T Easy, sequencing reactions were carried out using T7 primer (5'-TAATACGACTCACTATAGGG: SEQ ID No. 26) and using BigDye Terminator Cycle Sequencing Ready Reaction Kit v2.0 (Applied Biosystems Co.). Subsequently, the sequences were analyzed using ABI PRISM 310 Genetic Analyzer (Applied Biosystems Co.). As a result, base sequences of cDNAs encoding the H-chain and L-chain variable regions of the Dx3860 antibody gene and their deduced amino acid sequences (SEQ ID Nos. 1 and 2) as well as base sequences of cDNAs encoding the H-chain and L-chain variable regions of the Dx3150 antibody gene and their deduced amino acid sequences (SEQ ID Nos. 3 and 4) were obtained. The analysis of the base sequences as well as the deduction and analysis of the amino acid sequences were carried out using Analysis software DNAsis (Hitachi Soft Engineering Co.).

Also, the hypervariable domains contained in the sequences of SEQ ID Nos. 1-4 were identified according to the classification of ImMunoGeneTics data base (http://imgt.cines.fr). The data base is drawn up by referring to the articles by Lefranc, M.-P. et al. [Nucleic Acids Research, 27, p. 209-212 (1999)], Ruiz, M. et al. [Nucleic Acids Research, 28, p. 219-221 (2000)], and Lefranc, M.-P. [Nucleic Acids Research, 29, p. 207-209 (2001)]. The positions of the hypervariable domains (CDRs 1-3) identified are shown in FIGS. 1-4 together with the DNA sequences and amino acid sequences.

Construction of Expression Vector pET22Δ

Expression vector pET22Δ containing a T7/lac promoter, a histidine tag and a T7 terminator was constructed by replacing the sequence between restriction enzyme sites Xba I and Nco I of a commercially available vector: pET-22b(+) (Novagen Co.) with the sequence between restriction enzyme sites Xba I and Nco I of a commercially available vector: pET-3d (Novagen Co.). The expression vector pET22Δ was cleaved with restriction enzyme Nco I (New England BioLabs Co.) and Not I (Toyobo Co.), and the termini of the resultant fragments were dephosphated using Calf intestine Alkaline Phosphatase (Toyobo Co.). The bands of pET22Δ cleaved were separated by a 0.7% agarose gel electrophoresis, gels were excised, and DNAs were extracted from the gels using MagExtractor-PCR & Gel Clean Up-(Toyobo Co.). The following scFv fragments were integrated into this Nco I-Not I site as described below and the products were used as scFv expression vectors.

Construction of scFv Fragments from cDNAs

In order to link the cloned cDNAs of the H-chain and L-chain of the antibody gene via a DNA encoding a linker sequence and to integrate the product into an expression vector, the cDNAs of the H-chain and L-chain were amplified by the PCR using primers containing a sequence for a restriction enzyme,. For the Dx3150 H-chain, the primers were designed by modifying the sequence of the Bam HI site from GGATCC to GGATTC and including anterior and posterior sequences of the Bam HI site, and the amplification was carried out by dividing the H-chain DNA into two parts of 5'-side and 3'-side. In order to link the cDNAs of the H-chain and L-chain by filling-in, the linker DNAs were amplified by the PCR using primers containing part of these sequences. By this, for the single-chain antibody in which the H-chain is located at the amino-terminal side, the sequence of the 3'-terminal side of the H-chain sense DNA was ligated to the 5'-terminal side of the linker DNA, and the sequence of the 5'-terminal side of the L-chain sense DNA was ligated to the 3'-terminal side of the linker DNA. Also, for the single-chain antibody in which the L-chain is located at the amino-terminal side, the sequence of the 3'-terminal side of the L-chain sense DNA was ligated to the 5'-terminal side of the linker DNA, and the sequence of the 5'-terminal side of the H-chain sense DNA was ligated to the 3'-terminal side of the linker DNA. The combinations of the primers used for amplification of the H-chain, L-chain and linker DNA are shown in Table 6 and Table 7.

TABLE 6

PCR primers for construction of scFvs

Oligo for linker (sense)

GGA GGA GGC GGT TCA GGC GGA GGT GGC TCT GGC GGT GGC GGA TCC
(SEQ ID No. 27)

Dx3860 HL

H-chain
| 3860H 5' (Nco) | G ACC ATG GAA GTG AAG CTG GTG GAG TCC GGG GG (SEQ ID No. 28) |
| --- | --- |
| 3860H 3' (Mro) | CC TCC GGA AGA GAC AGT GAC CAG GGT ACC TTG GC (SEQ ID No. 29) |

L-chain
| 3860L 5' (Bam) | GC GGA TCC CAG GCT GTT GTG ACT CAG GAA TCT (SEQ ID No. 30) |
| --- | --- |
| 3860L 3' (Not) | G AGC GGC CGC GCC TAG GAC AGT CAG TTT GGT (SEQ ID No. 31) |

Linker extension
| Linker 5' (3860H) | GGT ACC CTG GTC ACT GTC TCT TCC GGA GGA GGC GGT TCA G (SEQ ID No. 32) |
| --- | --- |
| Linker 3' (3860L) | AGA TTC CTG AGT CAC AAC AGC CTG GAT CCG CCA CCG CCA G (SEQ ID No. 33) |

Dx3860 LH

L-chain
| 3860L 5' (Nco) | G ACC ATG GCC CAG GCT GTT GTG ACT CAG GAA TCT (SEQ ID No. 34) |
| --- | --- |
| 3860L 3' (Mro) | CC TCC GGA GCC TAG GAC AGT CAG TTT GGT TCC TCC (SEQ ID No. 35) |

H-chain
| 3860H 5' (Bam) | GC GGA TCC GAA GTG AAG CTG GTG GAG TCC GGG GGA GG (SEQ ID No. 36) |
| --- | --- |
| 3860H 3' (Not) | G AGC GGC CGC TGC AGA GAC AGT GAC CAG AGT (SEQ ID No. 37) |

Linker extension
| Linker 5' (3860L) | ACC AAA CTG ACT GTC CTA GGC TCC GGA GGA GGC GGT TCA G (SEQ ID No. 38) |
| --- | --- |

TABLE 6-continued

PCR primers for construction of scFvs

| | |
|---|---|
| Linker 3' (3860H) | CCC GGA CTC CAC CAG CTT CAC TTC GGA TCC GCC ACC GCC AG (SEQ ID No. 39) |

TABLE 7

PCR primers for construction of scFvs (Continued)

Dx3150 HL

H-chain (5'-side)
| | |
|---|---|
| 3150H 5' (Nco) | G ACC ATG GAT GTA CAG CTT CAG GAG TCA GGA CC (SEQ ID No. 40) |
| 3150H (128 at) | CC TGG AAA CTG CCG AAT CCA GTT CCA GT (SEQ ID No. 41) |

H-chain (3'-side)
| | |
|---|---|
| 3150H (101 sn) | AC TGG AAC TGG ATT CGG CAG TTT CCA GG (SEQ ID No. 42) |
| 3150H 3' (Mro) | CC TCC GGA GGA GAC TGT GAG AGT GGT ACC TTG GC (SEQ ID No. 43) |

L-chain
| | |
|---|---|
| 3150L 5' (Bam) | GC GGA TCC CAG GCT GTT GTG ACT CAG GAA TCT (SEQ ID No. 44) |
| 3150L 3' (Not) | G AGC GGC CGC GCC TAG GAC AGT CAG TCT GGT (SEQ ID No. 45) |

Linker extension
| | |
|---|---|
| Linker 5' (3150H) | GGT ACC ACT CTC ACA GTC TCC TCC GGA GGA GGC GGT TCA G (SEQ ID No. 46) |
| Linker 3' (3150L) | AGA TTC CTG AGT CAC AAC AGC TGG GGA TCC GCC ACC GCC AG (SEQ ID No. 47) |

Dx3150 LH

L-chain
| | |
|---|---|
| 3150L 5' (Nco) | G ACC ATG GCC CAG GCT GTT GTG ACT CAG GAA TCT (SEQ ID No. 48) |
| 3150L 3' (Mro) | CC TCC GGA GCC TAG GAC AGT CAG TCT GGT TCC TCC (SEQ ID No. 49) |

H-chain (5'-side)
| | |
|---|---|
| 3150H 5' (Bam) | GC GGA TCC GAT GTA CAG CTT CAG GAG TCA GGA CCT GG (SEQ ID No. 50) |
| 3150H (128 at) | CC TGG AAA CTG CCG AAT CCA GTT CCA GT (SEQ ID No. 51) |

H-chain (3'-side)
| | |
|---|---|
| 3150H (101 sn) | AC TGG AAC TGG ATT CGG CAG TTT CCA GG (SEQ ID No. 52) |
| 3150H 3' (Not) | G AGC GGC CGC TGA GGA GAC TGT GAG AGT GGT (SEQ ID No. 53) |

Linker extension
| | |
|---|---|
| Linker 5' (3150L) | ACC AGA CTG ACT GTC CTA GGC TCC GGA GGA GGC GGT TCA G (SEQ ID No. 54) |
| Linker 3' (3150H) | TCC TGA CTC CTG AAG CTG TAC ATC GGA TCC GCC ACC GCC AG (SEQ ID No. 55) |

The PCR amplification was carried out using GeneAmp PCR System 9700 (Applied Biosystems Co.) and using rTaq DNA polymerase (Toyobo Co.), as follows. Thus, the reaction cycle of 94° C.×1 minute, 58° C.×1 minute and 72° C.×1 minute was repeated 5 cycles and then the reaction cycle of 94° C.×1 minute, 48° C.×1 minute and 72° C.×1 minute 20 cycles. After the PCR amplification, each PCR product was separated by a 3% agarose gel electrophoresis. A part of gel containing a DNA fragment was excised, and the DNA was extracted from the gel using MagExtractor -PCR & Gel Clean Up- (Toyobo Co.). Subsequently, the three extracted DNAs of the H-chain, L-chain and linker DNA were mixed, and the H-chain, L-chain and linker DNA were ligated together by repeating 20 cycles the reaction cycle of 94° C.×1.5 minutes and 65° C.×3 minutes using rTaq DNA polymerase (Toyobo Co.), or 20 cycles the reaction cycle of 95° C.×1.5 minutes and 65° C.×6 minutes using Pfu DNA polymerase (STRATAGENE Co.).

The scFv fragments thus ligated are shown in FIGS. 5-8 together with the amino acid sequences encoded thereby (SEQ ID Nos. 56-59; or SEQ ID Nos. 60-63 for amino acid sequences only).

FIG. 5 (SEQ ID No. 56) shows the scFv fragment (Dx3860HL) containing the H-chain variable region of monoclonal antibody Dx3860, a linker, and the L-chain variable region of Dx3860 in this order starting from the N-terminal side, and positions 1-114 of the amino acid sequence shows the H-chain variable region, positions 115-129 the linker, and positions 130-239 the L-chain variable region.

FIG. 6 (SEQ ID No. 57) shows the scFv fragment (Dx3860LH) containing the L-chain variable region of monoclonal antibody Dx3860, a linker, and the H-chain variable region of Dx3860 in this order starting from the N-terminal side, and positions 1-110 of the amino acid sequence shows the L-chain variable region, positions 112-126 the linker, and positions 127-240 the H-chain variable region.

FIG. 7 (SEQ ID No. 58) shows the scFv fragment (Dx3150HL) containing the H-chain variable region of monoclonal antibody Dx3150, a linker, and the L-chain variable region of Dx3150 in this order starting from the N-terminal side, and positions 1-118 of the amino acid sequence shows the H-chain variable region, positions 119-133 the linker, and positions 134-243 the L-chain variable region.

FIG. 8 (SEQ ID No. 59) shows the scFv fragment (Dx3150LH) containing the L-chain variable region of monoclonal antibody Dx3150, a linker, and the H-chain variable region of Dx3150 in this order starting from the N-terminal side, and positions 1-110 of the amino acid sequence shows the L-chain variable region, positions 112-126 the linker, and positions 127-244 the H-chain variable region.

Furthermore, in order to amplify the resultant scFv fragment, the PCR was carried out by adding primers corresponding to both ends (Nco I-Not I) of the scFv to the reaction solution. For Dx3860, the reaction cycle of 94° C.×1 minute, 67° C.×1 minute and 72° C.×2 minutes was repeated 5 cycles, and then the reaction cycle of 94° C.×1 minute, 60° C.×1 minute and 72° C.×2 minutes 20 cycles. For Dx3150, the reaction cycle of 95° C.×1 minute, 62° C.×1 minute and 75° C.×4 minutes was repeated 5 cycles, and then the reaction cycle of 95° C.×1 minute, 55° C.×1 minute and 75° C.×4 minutes 20 cycles. The PCR products were separated by a 1.5% agarose gel electrophoresis, a part of gel containing a DNA fragment (730-740 bp) of the scFv was excised, and the DNA fragment was extracted from the gel. Subsequently, the termini of the DNA fragment were treated with restriction enzymes Nco I (New England BioLabs Co.) and Not I (Toyobo Co.), and the fragment was again purified using MagExtractor.

The scFv DNA fragment was inserted into the Nco I-Not I site of expression vector pET22Δ, and *Escherichia coli* XL1-Blue was transformed with the expression vector. DNA Ligetion Kit Ver.2 (Takara Shuzo Co.) was used for ligation, and XL1-Blue Competent Cells (STRATAGENE Co.) were used as competent cells. The clones subcloned were analyzed for the sequence of scFv part, and clones having a correct sequence were selected and used for the expression of the scFv. As described above, expression vector pET22Δ-Dx3860HL containing scFv fragment Dx3860HL as well as expression vector pET22Δ-Dx3150HL containing scFv fragment Dx3150HL were obtained.

Expression vector pET22Δ-Dx3860HL was introduced into *Escherichia coli* B and expression vector pET22Δ-Dx3150HL was introduced into *Escherichia coli* K-12. The resultant *Escherichia coli* B (pET22Δ-Dx3860HL) and *Escherichia coli* K-12 (pET22Δ-Dx3150HL) were deposited to International Patent Organism Depositary, National Institute of Advanced Industrial Science and Technology (AIST Tsukuba Central 6, 1-1, Higashi 1-chome Tsukuba-shi, Ibaraki-ken 305-8566 Japan) under the terms of the Budapest Treaty on Feb. 27, 2003, and obtained the accession numbers of FERM BP-8305 and FERM BP-8306, respectively.

Expression in *Escherichia coli*

*Escherichia coli* Origami B (DE3) (Novagen Co.) transformed with expression vector pET22Δ-Dx3860HL integrating scFv fragment Dx3860HL was cultivated in a LB medium (300 ml) at 37° C. until about 0.5 of OD600 was obtained. The temperature was then lowered to 25° C. and the cultivation was continued. When about 1.0 of OD600 was obtained, IPTG (isopropylthiogalactoside) was added to the culture until the final concentration of 1 mM, and the cultivation was continued overnight to induce the expression of the scFv. Cell bodies (about 1.0 g) were recovered by centrifugation and suspended in 50 mM tris-HCl (pH 8.0), 0.1 M NaCl. Then, lysozyme (final concentration 0.2 mg/ml) and Triton X-100 (final concentration 1%) were added to the suspension to effect the cell lysis. The precipitate was recovered by centrifugation (15,000×g, 20 minutes) and washed twice with a buffer containing 1.0% Triton X-100 to obtain about 100 mg of the precipitate containing the scFv.

Reconstitution of scFv

The scFv obtained as an inclusion body was added to a buffer of 25 mM PB, 350 mM NaCl and 6 M guanidine-HCl (pH 7.4), and dissolved by allowing it to stand overnight at 4° C. The residue was removed by centrifugation (10,000×g, 15 minutes), and the solution was then applied to a nickel-chelate column (Qiagen Co.) equilibrated with the above buffer. The column was thoroughly washed with the buffer in an amount of about 5-10 times of the column volume, and the buffer was then replaced with the above buffer containing 20% glycerol and 400 mM alginine. The scFv bound to the chelate column was reconstituted using a guanidine-HCl gradient of 6 M to 0 M. The column was washed with a solution (pH 7.4) of 25 mM PB, 350 mM NaCl, 20% glycerol, and 50 mM imidazole, and the scFv was then eluted by raising the imidazole concentration to 300 mM.

Determination of 2,3,4,7,8-PeCDF by an Indirect Competitive Immunoassay Using Anti-2,3,4,7,8-PeCDF scFv One μg/ml of 2,3,4,7,8-PeCDF derivative-BSA conjugate (50 μl) was added to a microtiter plate, and allowed to react at room temperature for one hour. The wells of the microtiter plate were washed with PBS(−) containing 0.05% Tween 20. A solution of Block Ace (Yukijirushi Co.) was then added to the wells, and the wells were blocked by allowing them to stand at room temperature for two hours. After the microtiter plate was washed, a solution (25 μl) of 2,3,4,7,8-PeCDF prepared in various concentrations (a solution in 20% DMSO) and a solution (25 μl) of anti-2,3,4,7,8-PeCDF scFv were added to the wells, and allowed to react at room temperature for 0.5 to 1 hour. After the microtiter plate was again washed, a solution of anti-tetra-His antibody (Qiagen Co.) 2000-fold diluted was added to the wells, and allowed to react at room temperature for one hour. Subsequently, a solution (50 μl) of peroxidase-labeled anti-mouse IgG (recognizing γ-chain) antibody (KPL Co.) 3000-fold diluted was added to the wells, and allowed to react at room temperature for one hour. After the wells of the microtiter plate were thoroughly washed to remove an unreacted solution, a substrate solution (TMB substrate, KPL Co.) was added to the wells and the plate was allowed to stand at room temperature for 15 minutes. The reaction was terminated by adding 1 M $H_3PO_4$ (50 μl), and OD450 (control: OD600) was measured using a plate reader (Labsystems Co.). The results are shown in FIG. 9 as a graph. It is evident from the graph that 2,3,4,7,8-PeCDF can be determined in a highly sensitive manner using the anti-2,3,4,7,8-PeCDF scFv.

Confirmation of 2,3,4,7,8-PeCDF Binding Activity of H-Chain Variable Region Polypeptide

*Escherichia coli* Origami B (DE3) (Novagen Co.) was transformed using expression vector pET22Δ-Dx3860H which was prepared by removing the sequence between restriction enzyme sites Bam HI and Not I containing the L-chain variable region of expression vector pET22Δ-Dx3860HL. Using the transformant, the expression of the H-chain variable region polypeptide (polypeptide having the amino acid sequence as shown in SEQ ID No. 5) was carried out in the same manner as in the case of the scFv.

Figure 10:
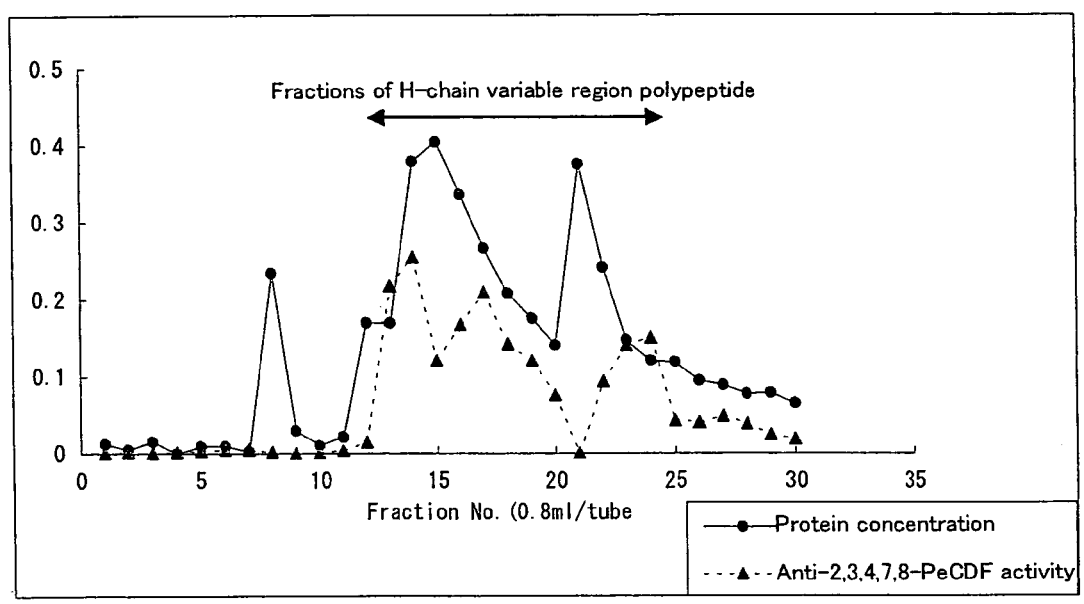
FIG. 10 represents a graph showing the relationship of H-chain variable region polypeptide fractions with anti-2,3,4,7,8-PeCDF activity.

The H-chain variable region polypeptide obtained as an inclusion body was reconstituted on a nickel-chelate column as described above, and the product was then isolated and purified using imidazole. Protein concentrations of the fractions eluted from the chelate column were determined by measuring absorbance (280 nm), and the reactivity to an immobilized 2,3,4,7,8-PeCDF-BSA conjugate was also investigated by an EIA method. As a result, it was recognized that the fractions of the H-chain variable region polypeptide have an anti-2,3,4,7,8-PeCDF activity as shown in FIG. 10. Thus, it was confirmed that the H-chain variable region polypeptide has a binding activity to 2,3,4,7,8-PeCDF.

Introduction of Mutation into H-Chain and Confirmation of 2,3,4,7,8-PeCDF Binding Activity of the Mutant A library of mutation-introduced antibody genes was prepared on the basis of the gene sequence of monoclonal antibody Dx3860. The mutation was introduced by an error-prone PCR using the gene of the H-chain variable region ($V_H$) of the antibody as a template and using primers prepared by adding restriction enzyme sites to the sequences of 5'-side and 3'-side. The error-prone PCR is a method of introducing random mutations by utilizing the property of the Taq DNA polymerase often causing reading-errors during amplification and by intentionally inducing the reading-errors during the PCR by the addition of manganese chloride. The PCR products were terminus-treated with restriction enzymes and purified, and the products were substituted for the H-chain gene of a phagemid expressing a single-chain antibody using the restriction enzyme sites. The resultant phagemids were used to transform *Escherichia coli* TG1.

To a culture (10 ml) of *E. coli* transformed, ampicillin was added in a final concentration of 100 μg/ml and M13KO7 phage in a final concentration $4\times10^9$ pfu/ml, and cultivation was carried out at 37° C. for one hour. The cell bodies were recovered by centrifugation, resuspended in a 2× YT medium (10 ml) containing 100 μg/ml ampicillin and 50 μg/ml kanamycin, and cultivated at 37° C. overnight to produce single-chain antibody-displaying phages in the medium. The culture was centrifuged, and a 20% polyethylene glycol solution (2 ml) containing 2.5 M NaCl was added to and mixed with the supernatant (10 ml) of the culture excluding the *E. coli* cell bodies. The mixture was allowed to stand on ice for one hour, and then centrifuged (1000 g×20 minutes) under cooling. After the supernatant was fully removed, the remaining precipitate was dissolved in a solution (1 ml) of Block Ace (Yukijirushi Co.) 10-fold diluted, and the resultant solution was used as a solution of single-chain antibody-displaying phages.

Subsequently, biopanning was carried out in order to concentrate clones having a high reactivity to a 2,3,4,7,8-PeCDF derivative, a 2,3,7,8-TCDF derivative, and a chlorobenzene derivative from the single-chain antibody-displaying phages prepared. The phage solution prepared was firstly preincubated in a microtiter plate to which only a blocking agent was immobilized (100 μl/well, at room temperature for one hour) to exclude a nonspecific binding. The phage solution was then transferred to a microtiter plate to which respective BSA conjugates of a 2,3,4,7,8-PeCDF derivative, a 2,3,7,8-TCDF derivative, and a chlorobenzene derivative were immobilized and which was blocked with a solution of Block Ace (100 μl/well), and allowed to react at room temperature for one hour in the presence of 8% DMSO. After the reaction, PBS(−) containing 8% DMSO and 0.1% Tween 20 (300 μl) was added to the wells of the plate, and pipetting was carried out. The plate was allowed to stand for 5 minutes, and the washing buffer was then discarded. After the washing procedure was repeated three times, the washing buffer was fully removed. Then, 0.1 M glycine-HCl buffer (pH 2.2) (100 μl/well) was added to the wells, and the plate was allowed to stand for 10 minutes. After pipetting, the single-chain antibody-displaying phages liberated from the immobilized antigens were recovered and immediately neutralized by adding a tris solution (pH 8.0).

The phage solution recovered by biopanning was mixed with a culture of *E. coli* TG1($OD_{600\ nm}$=0.3) cultivated in a 2× YT medium (2.5 ml), and the mixture was cultivated at 37° C. for one hour to effect reinfection with the phage. Subsequently, M13KO7 phage was added in a final concentration $4\times10^9$ pfu/ml to a culture containing ampicillin (final concentration 100 μg/ml) and glucose (final concentration 2%), and further cultivation was carried out at 37° C. for one hour. The cell bodies were recovered by centrifugation, resuspended in a 2× YT medium (10 ml) containing 100 μg/ml ampicillin and 50 μg/ml kanamycin, and cultivated at 37° C. overnight. By the above procedures, single-chain antibody-displaying phages were amplified and produced in a medium (phage rescue). The phages amplified were again recovered by polyethylene glycol precipitation. The concentration and reinfection by the biopanning as well as the amplification by the phage rescue were repeated three to five times.

Figures 11, 12:
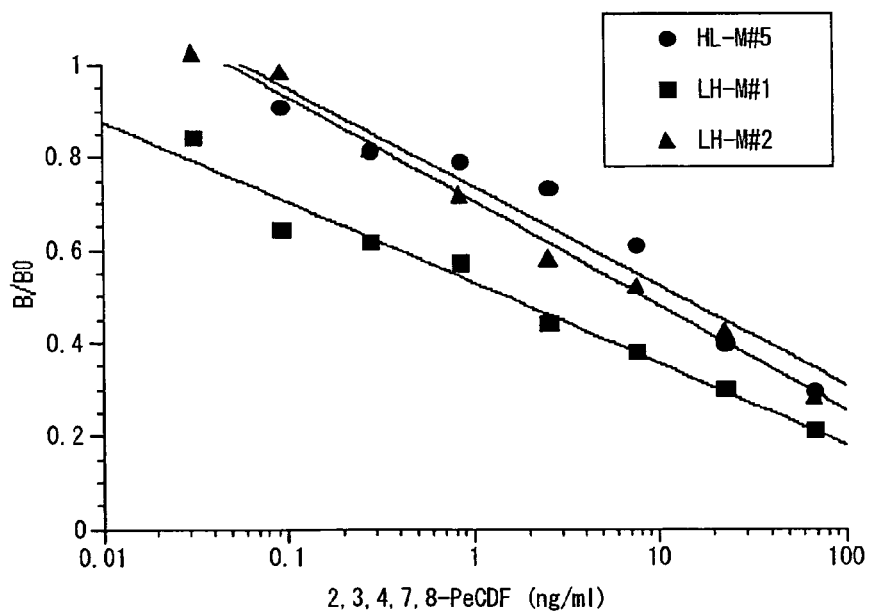
FIG. 11 shows the amino acid sequences of H-chain variable region mutants of monoclonal antibody Dx3860.
FIG. 12 represents a graph showing the results of determining 2,3,4,7,8-PeCDF using mutation-introduced Dx3860 scFv-displaying phages.

*E. coli* TG1 was infected with phage clones regarded as concentrated sufficiently, plated on an agar plate, and cultivated at 30° C. overnight to form single colonies. Six clones were selected at random from the single colonies of TG1 every screening conditions, phagemids were prepared by a conventional method, and the sequencing reaction with BigDye Terminator Cycle Sequencing Ready Reaction Kit v3.0 (Applied Biosystems Co.) was carried out using the phagemids as a template. The base sequences were analyzed with ABI PRISM 310 Genetic Analyzer (Applied Biosystems Co.), and 4 kinds of mutants having mutations in the H-chain variable region (Dx3860HL-M#5, Dx3860LH-M#1, Dx3860LH-M#2, Dx3860LH-M#3) were obtained. The amino acid sequences of these mutants having mutations in the H-chain variable region are shown in FIG. 11 and SEQ ID Nos. 64-67. In comparison with the H-chain variable region of wild-type Dx3860, 1 or 2 mutations of amino acids were observed. Furthermore, mutation-introduced positions were not limited to CDR sites but observed in the framework as well.

It was confirmed that all the mutants recognize 2,3,4,7,8-PeCDF by an indirect competitive immunoassay (FIG. 12). Also, it was found that there is a difference in the antibody titer and reactivity in DMSO and the mutants show superior results over the wild-type in both the antibody titer and stability in DMSO (FIG. 13 and FIG. 14). Moreover, the tendency was retained in each scFv expressed by *E. coli* Origami B (DE3) transformed.

INDUSTRIAL AVAILABILITY

It is possible to prepare a recombinant antibody recognizing 2,3,4,7,8-PeCDF in a large amount by using a DNA provided by the present invention to express the antibody in host cells. The recombinant antibody thus prepared is cheaper than the parent monoclonal antibody. The present recombinant antibody can be used for capturing 2,3,4,7,8-PeCDF immunologically and applied to an immunoassay. Also, using a DNA into which a mutation is introduced, it is possible to prepare a recombinant antibody having a further advantageous property, for example, a recombinant antibody having an improved affinity for 2,3,4,7,8-PeCDF or a recombinant antibody having an improved stability, and to solve various problems associated with naturally occurring antibody proteins.

The invention claimed is:

1. A recombinant antibody having a binding activity to 2,3,4,7,8-pentachlorodibenzofuran (2,3,4,7,8-PeCDF), which comprises a variable heavy chain or a variable light chain selected from the group consisting of:
   (1) a variable heavy chain having the amino acid sequence as shown in SEQ ID No. 5;
   (2) a variable light chain having the amino acid sequence as shown in SEQ ID No. 6;
   (3) a variable heavy chain having the amino acid sequence as shown in SEQ ID No. 7;
   (4) a variable light chain having the amino acid sequence as shown in SEQ ID No. 8; and
   (5) a variable heavy chain having the amino acid sequence as shown in any one of SEQ ID Nos. 64-67 and having a binding activity to 2,3,4,7,8-PeCDF.

2. A recombinant antibody which comprises:
   a variable heavy chain region having the amino acid sequence as shown in SEQ ID No. 5, or any one of amino acid sequences as shown in SEQ ID Nos. 64-67 and having a binding activity to 2,3,4,7,8-PeCDF; and
   a variable light chain region having the amino acid sequence as shown in SEQ ID No. 6.

3. A recombinant antibody which comprises:
   a variable heavy chain region having the amino acid sequence as shown in SEQ ID No. 7; and
   variable light chain region having the amino acid sequence as shown in SEQ ID No. 8.

4. A DNA encoding the amino acid sequence of the recombinant antibody according to claim 1.

5. A cloning or expression vector comprising the DNA according to claim 4.

6. A transformant transformed with the cloning or expression vector according to claim 5.

7. A process for preparing a recombinant antibody, which comprises cultivating the transformant transformed with an expression vector according to claim 6 in a suitable medium, and recovering the recombinant antibody from the transformant or the medium.

8. A method for immunologically capturing 2,3,4,7,8-PeCDF, which comprises binding of the recombinant antibody according to claim 1, to 2,3,4,7,8-PeCDF.

9. A method for immunologically determining 2,3,4,7,8-PeCDF in a sample, which comprises binding of the recombinant antibody according to claim 1, to 2,3,4,7,8-PeCDF.

* * * * *

```
                            SEQUENCE LISTING

<160> NUMBER OF SEQ ID NOS: 67

<210> SEQ ID NO 1
<211> LENGTH: 342
<212> TYPE: DNA
<213> ORGANISM: Unknown
<220> FEATURE:
<223> OTHER INFORMATION: DNA encoding polypeptide of H-chain variable
      region of monoclonal antibody Dx 3860
<220> FEATURE:
<221> NAME/KEY: exon
<222> LOCATION: (1)..(342)

<400> SEQUENCE: 1 gaa gtg aag ctg gtg gag tct ggg gga ggc tta gtg aag cct gga ggg      48
Glu Val Lys Leu Val Glu Ser Gly Gly Gly Leu Val Lys Pro Gly Gly
1               5                   10                  15 tcc ctg aaa ctc tcc tgt gca gcc tct gga ttc act ttc agt tcc tat      96
Ser Leu Lys Leu Ser Cys Ala Ala Ser Gly Phe Thr Phe Ser Ser Tyr
            20                  25                  30 gcc atg tct tgg gtt cgc cag act cca gag aag agg ctg gag tgg gtc     144
Ala Met Ser Trp Val Arg Gln Thr Pro Glu Lys Arg Leu Glu Trp Val
        35                  40                  45 gca tcc ttt agt aat ggt ggt atc acc tac tat cca gac agt gtg aag     192
Ala Ser Phe Ser Asn Gly Gly Ile Thr Tyr Tyr Pro Asp Ser Val Lys
    50                  55                  60 ggc cga ttc acc atc tcc aga gat aat gcc agg aac atc ctg tac ctg     240
Gly Arg Phe Thr Ile Ser Arg Asp Asn Ala Arg Asn Ile Leu Tyr Leu
65                  70                  75                  80 caa atg acc agt ctg agg tct gag gac acg gcc att tat tac tgt gca     288
Gln Met Thr Ser Leu Arg Ser Glu Asp Thr Ala Ile Tyr Tyr Cys Ala
                85                  90                  95 aga ggc tat ggt cct gct tac tgg ggc caa ggg act ctg gtc act gtc     336
Arg Gly Tyr Gly Pro Ala Tyr Trp Gly Gln Gly Thr Leu Val Thr Val
            100                 105                 110 tct gca                                                              342
Ser Ala <210> SEQ ID NO 2
<211> LENGTH: 330
<212> TYPE: DNA
<213> ORGANISM: Unknown
<220> FEATURE:
<223> OTHER INFORMATION: DNA encoding polypeptide of L-chain variable
      region of monoclonal antibody Dx 3860
<220> FEATURE:
<221> NAME/KEY: exon
<222> LOCATION: (1)..(330)

<400> SEQUENCE: 2 cag gct gtt gtg act cag gaa tct gca ctc acc aca tca cct ggt gaa      48
Gln Ala Val Val Thr Gln Glu Ser Ala Leu Thr Thr Ser Pro Gly Glu
1               5                   10                  15 aca gtc aca ctc act tgt cgc tca agt act ggg gct gtt aca act ctt      96
```

```
Thr Val Thr Leu Thr Cys Arg Ser Ser Thr Gly Ala Val Thr Thr Leu
         20                  25                  30 aac tat gcc aac tgg gtc caa gaa aaa cca gat cat tta ttc act ggt      144
Asn Tyr Ala Asn Trp Val Gln Glu Lys Pro Asp His Leu Phe Thr Gly
             35                  40                  45 cta ata ggt aat acc aac aac cga gct cca ggt gtt cct gcc aga ttc      192
Leu Ile Gly Asn Thr Asn Asn Arg Ala Pro Gly Val Pro Ala Arg Phe
         50                  55                  60 tca ggc tcc ctg att gga gac aag gct gcc ctc acc atc aca ggg gca      240
Ser Gly Ser Leu Ile Gly Asp Lys Ala Ala Leu Thr Ile Thr Gly Ala
65                  70                  75                  80 cag act gag gat gag gca ata tat ttc tgt gct cta tgg tac agc aac      288
Gln Thr Glu Asp Glu Ala Ile Tyr Phe Cys Ala Leu Trp Tyr Ser Asn
                 85                  90                  95 cat ttg gtg ttc ggt gga gga acc aaa ctg act gtc cta ggc              330
His Leu Val Phe Gly Gly Gly Thr Lys Leu Thr Val Leu Gly
             100                 105                 110

<210> SEQ ID NO 3
<211> LENGTH: 354
<212> TYPE: DNA
<213> ORGANISM: Unknown
<220> FEATURE:
<223> OTHER INFORMATION: DNA encoding polypeptide of H-chain variable
      region of monoclonal antibody Dx 3150
<220> FEATURE:
<221> NAME/KEY: exon
<222> LOCATION: (1)..(354)

<400> SEQUENCE: 3 gat gta cag ctt cag gag tca gga cct ggc ctc gtg aaa cct tct cag       48
Asp Val Gln Leu Gln Glu Ser Gly Pro Gly Leu Val Lys Pro Ser Gln
1               5                  10                  15 tct ctg tct ctc acc tgt tct gtc act ggc tac tcc atc acc agt ggc       96
Ser Leu Ser Leu Thr Cys Ser Val Thr Gly Tyr Ser Ile Thr Ser Gly
             20                  25                  30 ttt tac tgg aac tgg atc cgg cag ttt cca gga aac aaa ctg gaa tgg      144
Phe Tyr Trp Asn Trp Ile Arg Gln Phe Pro Gly Asn Lys Leu Glu Trp
             35                  40                  45 atg ggc tac ata agc tac gac ggt tac aat aat tac aac cca ttt ctc      192
Met Gly Tyr Ile Ser Tyr Asp Gly Tyr Asn Asn Tyr Asn Pro Phe Leu
         50                  55                  60 aaa aat cga gtg tcc atc act cgt gac aca tct gag aac cag ttt ttc      240
Lys Asn Arg Val Ser Ile Thr Arg Asp Thr Ser Glu Asn Gln Phe Phe
65                  70                  75                  80 ctg aag ttg cat tct gtg act act gag gac aca gct aca tat tac tgt      288
Leu Lys Leu His Ser Val Thr Thr Glu Asp Thr Ala Thr Tyr Tyr Cys
                 85                  90                  95 gta agt tac ggt agt cgg agg gga gtt acc tac tgg ggc caa ggc acc      336
Val Ser Tyr Gly Ser Arg Arg Gly Val Thr Tyr Trp Gly Gln Gly Thr
             100                 105                 110 act ctc aca gtc tcc tca                                              354
Thr Leu Thr Val Ser Ser
        115

<210> SEQ ID NO 4
<211> LENGTH: 330
<212> TYPE: DNA
<213> ORGANISM: Unknown
<220> FEATURE:
<223> OTHER INFORMATION: DNA encoding polypeptide of L-chain variable
      region of monoclonal antibody Dx 3150
<220> FEATURE:
<221> NAME/KEY: exon
```

<222> LOCATION: (1)..(330)

<400> SEQUENCE: 4

```
cag gct gtt gtg act cag gaa tct gca ctc acc aca tca cct ggt gaa      48
Gln Ala Val Val Thr Gln Glu Ser Ala Leu Thr Thr Ser Pro Gly Glu
1               5                   10                  15 aca gtc aca ctc act tgt cgc tca agt act ggg gct gtt aca act agt      96
Thr Val Thr Leu Thr Cys Arg Ser Ser Thr Gly Ala Val Thr Thr Ser
                20                  25                  30 aac tat gcc aac tgg gtc caa gaa aaa cca gat cat tta ttc act ggt     144
Asn Tyr Ala Asn Trp Val Gln Glu Lys Pro Asp His Leu Phe Thr Gly
            35                  40                  45 cta ata ggt aat acc aac aac cga gct cca ggt gtt cct gcc aga ttc     192
Leu Ile Gly Asn Thr Asn Asn Arg Ala Pro Gly Val Pro Ala Arg Phe
        50                  55                  60 tct ggc tcc ctg att gga gac aag gct gcc ctc acc atc aca ggg gca     240
Ser Gly Ser Leu Ile Gly Asp Lys Ala Ala Leu Thr Ile Thr Gly Ala
65                  70                  75                  80 cag act gag gat gag gcg ata tat ttc tgt gct ctt tgg tac aac acc     288
Gln Thr Glu Asp Glu Ala Ile Tyr Phe Cys Ala Leu Trp Tyr Asn Thr
                85                  90                  95 cat ttg gtg ttc ggt gga gga acc aga ctg act gtc cta ggc             330
His Leu Val Phe Gly Gly Gly Thr Arg Leu Thr Val Leu Gly
                100                 105                 110
```

<210> SEQ ID NO 5
<211> LENGTH: 114
<212> TYPE: PRT
<213> ORGANISM: Unknown
<220> FEATURE:
<223> OTHER INFORMATION: Polypeptide of H-chain variable region of monoclonal antibody Dx 3860

<400> SEQUENCE: 5

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Ser Phe Ser Asn Gly Gly Ile Thr Tyr Tyr Pro Asp Ser Val Lys
        50                  55                  60

Gly Arg Phe Thr Ile Ser Arg Asp Asn Ala Arg Asn Ile Leu Tyr Leu
65                  70                  75                  80

Gln Met Thr Ser Leu Arg Ser Glu Asp Thr Ala Ile Tyr Tyr Cys Ala
                85                  90                  95

Arg Gly Tyr Gly Pro Ala Tyr Trp Gly Gln Gly Thr Leu Val Thr Val
                100                 105                 110

Ser Ala
```

<210> SEQ ID NO 6
<211> LENGTH: 110
<212> TYPE: PRT
<213> ORGANISM: Unknown
<220> FEATURE:
<223> OTHER INFORMATION: Polypeptide of L-chain variable region of monoclonal antibody Dx 3860

<400> SEQUENCE: 6

```
Gln Ala Val Val Thr Gln Glu Ser Ala Leu Thr Thr Ser Pro Gly Glu
1               5                   10                  15
```

Thr Val Thr Leu Thr Cys Arg Ser Ser Thr Gly Ala Val Thr Thr Leu
            20                  25                  30

Asn Tyr Ala Asn Trp Val Gln Glu Lys Pro Asp His Leu Phe Thr Gly
        35                  40                  45

Leu Ile Gly Asn Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Leu Val Phe Gly Gly Gly Thr Lys Leu Thr Val Leu Gly
            100                 105                 110

<210> SEQ ID NO 7
<211> LENGTH: 118
<212> TYPE: PRT
<213> ORGANISM: Unknown
<220> FEATURE:
<223> OTHER INFORMATION: Polypeptide of H-chain variable region of
      monoclonal antibody Dx 3150

<400> SEQUENCE: 7

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Phe Tyr Trp Asn Trp Ile Arg Gln Phe Pro Gly Asn Lys Leu Glu Trp
        35                  40                  45

Met Gly Tyr Ile Ser Tyr Asp Gly Tyr Asn Asn Tyr Asn Pro Phe Leu
    50                  55                  60

Lys Asn Arg Val Ser Ile Thr Arg Asp Thr Ser Glu Asn Gln Phe Phe
65                  70                  75                  80

Leu Lys Leu His Ser Val Thr Thr Glu Asp Thr Ala Thr Tyr Tyr Cys
                85                  90                  95

Val Ser Tyr Gly Ser Arg Arg Gly Val Thr Tyr Trp Gly Gln Gly Thr
            100                 105                 110

Thr Leu Thr Val Ser Ser
        115

<210> SEQ ID NO 8
<211> LENGTH: 110
<212> TYPE: PRT
<213> ORGANISM: Unknown
<220> FEATURE:
<223> OTHER INFORMATION: Polypeptide of L-chain variable region of
      monoclonal antibody Dx 3150

<400> SEQUENCE: 8

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Asn Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

```
Gln Thr Glu Asp Glu Ala Ile Tyr Phe Cys Ala Leu Trp Tyr Asn Thr
                85                  90                  95

His Leu Val Phe Gly Gly Gly Thr Arg Leu Thr Val Leu Gly
            100                 105                 110

<210> SEQ ID NO 9
<211> LENGTH: 8
<212> TYPE: PRT
<213> ORGANISM: Unknown
<220> FEATURE:
<223> OTHER INFORMATION: Peptide of CDR 1 in H-chain variable region of
      monoclonal antibody Dx 3860

<400> SEQUENCE: 9

Gly Phe Thr Phe Ser Ser Tyr Ala
1               5

<210> SEQ ID NO 10
<211> LENGTH: 7
<212> TYPE: PRT
<213> ORGANISM: Unknown
<220> FEATURE:
<223> OTHER INFORMATION: Peptide of CDR 2 in H-chain variable region of
      monoclonal antibody Dx 3860

<400> SEQUENCE: 10

Phe Ser Asn Gly Gly Ile Thr
1               5

<210> SEQ ID NO 11
<211> LENGTH: 8
<212> TYPE: PRT
<213> ORGANISM: Unknown
<220> FEATURE:
<223> OTHER INFORMATION: Peptide of CDR 3 in H-chain variable region of
      monoclonal antibody Dx 3860

<400> SEQUENCE: 11

Ala Arg Gly Tyr Gly Pro Ala Tyr
1               5

<210> SEQ ID NO 12
<211> LENGTH: 9
<212> TYPE: PRT
<213> ORGANISM: Unknown
<220> FEATURE:
<223> OTHER INFORMATION: Peptide of CDR 1 in L-chain variable region of
      monoclonal antibody Dx 3860

<400> SEQUENCE: 12

Thr Gly Ala Val Thr Thr Leu Asn Tyr
1               5

<210> SEQ ID NO 13
<211> LENGTH: 8
<212> TYPE: PRT
<213> ORGANISM: Unknown
<220> FEATURE:
<223> OTHER INFORMATION: Peptide of CDR 3 in L-chain variable region of
      monoclonal antibody Dx 3860

<400> SEQUENCE: 13

Ala Leu Trp Tyr Ser Asn His Leu
1               5

<210> SEQ ID NO 14
```

```
<211> LENGTH: 9
<212> TYPE: PRT
<213> ORGANISM: Unknown
<220> FEATURE:
<223> OTHER INFORMATION: Peptide of CDR 1 in H-chain variable region of
      monoclonal antibody Dx 3150

<400> SEQUENCE: 14

Gly Tyr Ser Ile Thr Ser Gly Phe Tyr
1               5

<210> SEQ ID NO 15
<211> LENGTH: 7
<212> TYPE: PRT
<213> ORGANISM: Unknown
<220> FEATURE:
<223> OTHER INFORMATION: Peptide of CDR 2 in H-chain variable region of
      monoclonal antibody Dx 3150

<400> SEQUENCE: 15

Ile Ser Tyr Asp Gly Tyr Asn
1               5

<210> SEQ ID NO 16
<211> LENGTH: 11
<212> TYPE: PRT
<213> ORGANISM: Unknown
<220> FEATURE:
<223> OTHER INFORMATION: Peptide of CDR 3 in H-chain variable region of
      monoclonal antibody Dx 3150

<400> SEQUENCE: 16

Val Ser Tyr Gly Ser Arg Arg Gly Val Thr Tyr
1               5                   10

<210> SEQ ID NO 17
<211> LENGTH: 9
<212> TYPE: PRT
<213> ORGANISM: Unknown
<220> FEATURE:
<223> OTHER INFORMATION: Peptide of CDR 1 in L-chain variable region of
      monoclonal antibody Dx 3150

<400> SEQUENCE: 17

Thr Gly Ala Val Thr Thr Ser Asn Tyr
1               5

<210> SEQ ID NO 18
<211> LENGTH: 9
<212> TYPE: PRT
<213> ORGANISM: Unknown
<220> FEATURE:
<223> OTHER INFORMATION: Peptide of CDR 3 in L-chain variable region of
      monoclonal antibody Dx 3150

<400> SEQUENCE: 18

Ala Leu Trp Tyr Asn Thr His Leu Val
1               5

<210> SEQ ID NO 19
<211> LENGTH: 33
<212> TYPE: DNA
<213> ORGANISM: Artificial
<220> FEATURE:
<223> OTHER INFORMATION: Primer

<400> SEQUENCE: 19
gggaattcat grasttskgg ytmarctkgr ttt                                    33
```

<210> SEQ ID NO 20
<211> LENGTH: 36
<212> TYPE: DNA
<213> ORGANISM: Artificial
<220> FEATURE:
<223> OTHER INFORMATION: Primer

<400> SEQUENCE: 20
actagtcgac atggrcagrc ttacwtyytc attcct                          36

<210> SEQ ID NO 21
<211> LENGTH: 36
<212> TYPE: DNA
<213> ORGANISM: Artificial
<220> FEATURE:
<223> OTHER INFORMATION: Primer

<400> SEQUENCE: 21
actagtcgac atgatggtgt taagtcttct gtacct                          36

<210> SEQ ID NO 22
<211> LENGTH: 36
<212> TYPE: DNA
<213> ORGANISM: Artificial
<220> FEATURE:
<223> OTHER INFORMATION: Primer

<400> SEQUENCE: 22
actagtcgac atgggatgga gctrtatcat sytctt                          36

<210> SEQ ID NO 23
<211> LENGTH: 35
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (30)..(30)
<223> OTHER INFORMATION: inosine

<400> SEQUENCE: 23
cccaagcttc cagggrccar kggataracn grtgg                           35

<210> SEQ ID NO 24
<211> LENGTH: 33
<212> TYPE: DNA
<213> ORGANISM: Artificial
<220> FEATURE:
<223> OTHER INFORMATION: Primer

<400> SEQUENCE: 24
gggaattcat ggcctggayt ycwctywtmy tct                             33

<210> SEQ ID NO 25
<211> LENGTH: 32
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (24)..(24)
<223> OTHER INFORMATION: inosine

<400> SEQUENCE: 25

```
cccaagctta gctcytcwgw gganggyggr aa                                          32
```

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26

```
taatacgact cactataggg                                                       20
```

<210> SEQ ID NO 27
<211> LENGTH: 45
<212> TYPE: DNA
<213> ORGANISM: Artificial
<220> FEATURE:
<223> OTHER INFORMATION: Linker

<400> SEQUENCE: 27

```
ggaggaggcg gttcaggcgg aggtggctct ggcggtggcg gatcc                           45
```

<210> SEQ ID NO 28
<211> LENGTH: 33
<212> TYPE: DNA
<213> ORGANISM: Artificial
<220> FEATURE:
<223> OTHER INFORMATION: Primer

<400> SEQUENCE: 28

```
gaccatggaa gtgaagctgg tggagtccgg ggg                                        33
```

<210> SEQ ID NO 29
<211> LENGTH: 34
<212> TYPE: DNA
<213> ORGANISM: Artificial
<220> FEATURE:
<223> OTHER INFORMATION: Primer

<400> SEQUENCE: 29

```
cctccggaag agacagtgac cagggtacct tggc                                       34
```

<210> SEQ ID NO 30
<211> LENGTH: 32
<212> TYPE: DNA
<213> ORGANISM: Artificial
<220> FEATURE:
<223> OTHER INFORMATION: Primer

<400> SEQUENCE: 30

```
gcggatccca ggctgttgtg actcaggaat ct                                         32
```

<210> SEQ ID NO 31
<211> LENGTH: 31
<212> TYPE: DNA
<213> ORGANISM: Artificial
<220> FEATURE:
<223> OTHER INFORMATION: Primer

<400> SEQUENCE: 31

```
gagcggccgc gcctaggaca gtcagtttgg t                                          31
```

<210> SEQ ID NO 32
<211> LENGTH: 40
<212> TYPE: DNA
<213> ORGANISM: Artificial

```
<220> FEATURE:
<223> OTHER INFORMATION: Primer

<400> SEQUENCE: 32
ggtaccctgg tcactgtctc ttccggagga ggcggttcag                                40

<210> SEQ ID NO 33
<211> LENGTH: 41
<212> TYPE: DNA
<213> ORGANISM: Artificial
<220> FEATURE:
<223> OTHER INFORMATION: Primer

<400> SEQUENCE: 33
agattcctga gtcacaacag cctgggatcc gccaccgcca g                              41

<210> SEQ ID NO 34
<211> LENGTH: 34
<212> TYPE: DNA
<213> ORGANISM: Artificial
<220> FEATURE:
<223> OTHER INFORMATION: Primer

<400> SEQUENCE: 34
gaccatggcc caggctgttg tgactcagga atct                                     34

<210> SEQ ID NO 35
<211> LENGTH: 35
<212> TYPE: DNA
<213> ORGANISM: Artificial
<220> FEATURE:
<223> OTHER INFORMATION: Primer

<400> SEQUENCE: 35
cctccggagc ctaggacagt cagtttggtt cctcc                                    35

<210> SEQ ID NO 36
<211> LENGTH: 37
<212> TYPE: DNA
<213> ORGANISM: Artificial
<220> FEATURE:
<223> OTHER INFORMATION: Primer

<400> SEQUENCE: 36
gcggatccga agtgaagctg gtggagtccg ggggagg                                  37

<210> SEQ ID NO 37
<211> LENGTH: 31
<212> TYPE: DNA
<213> ORGANISM: Artificial
<220> FEATURE:
<223> OTHER INFORMATION: Primer

<400> SEQUENCE: 37
gagcggccgc tgcagagaca gtgaccagag t                                        31

<210> SEQ ID NO 38
<211> LENGTH: 40
<212> TYPE: DNA
<213> ORGANISM: Artificial
<220> FEATURE:
<223> OTHER INFORMATION: Primer

<400> SEQUENCE: 38
accaaactga ctgtcctagg ctccggagga ggcggttcag                               40
```

<210> SEQ ID NO 39
<211> LENGTH: 41
<212> TYPE: DNA
<213> ORGANISM: Artificial
<220> FEATURE:
<223> OTHER INFORMATION: Primer

<400> SEQUENCE: 39
cccggactcc accagcttca cttcggatcc gccaccgcca g           41

<210> SEQ ID NO 40
<211> LENGTH: 33
<212> TYPE: DNA
<213> ORGANISM: Artificial
<220> FEATURE:
<223> OTHER INFORMATION: Primer

<400> SEQUENCE: 40
gaccatggat gtacagcttc aggagtcagg acc                    33

<210> SEQ ID NO 41
<211> LENGTH: 28
<212> TYPE: DNA
<213> ORGANISM: Artificial
<220> FEATURE:
<223> OTHER INFORMATION: Primer

<400> SEQUENCE: 41
cctggaaact gccgaatcca gttccagt                          28

<210> SEQ ID NO 42
<211> LENGTH: 28
<212> TYPE: DNA
<213> ORGANISM: Artificial
<220> FEATURE:
<223> OTHER INFORMATION: Primer

<400> SEQUENCE: 42
actggaactg gattcggcag tttccagg                          28

<210> SEQ ID NO 43
<211> LENGTH: 34
<212> TYPE: DNA
<213> ORGANISM: Artificial
<220> FEATURE:
<223> OTHER INFORMATION: Primer

<400> SEQUENCE: 43
cctccggagg agactgtgag agtggtacct tggc                   34

<210> SEQ ID NO 44
<211> LENGTH: 32
<212> TYPE: DNA
<213> ORGANISM: Artificial
<220> FEATURE:
<223> OTHER INFORMATION: Primer

<400> SEQUENCE: 44
gcggatccca ggctgttgtg actcaggaat ct                     32

<210> SEQ ID NO 45
<211> LENGTH: 31
<212> TYPE: DNA
<213> ORGANISM: Artificial
<220> FEATURE:
<223> OTHER INFORMATION: Primer

<400> SEQUENCE: 45
gagcggccgc gcctaggaca gtcagtctgg t          31

<210> SEQ ID NO 46
<211> LENGTH: 40
<212> TYPE: DNA
<213> ORGANISM: Artificial
<220> FEATURE:
<223> OTHER INFORMATION: Primer

<400> SEQUENCE: 46
ggtaccactc tcacagtctc ctccggagga ggcggttcag     40

<210> SEQ ID NO 47
<211> LENGTH: 41
<212> TYPE: DNA
<213> ORGANISM: Artificial
<220> FEATURE:
<223> OTHER INFORMATION: Primer

<400> SEQUENCE: 47
agattcctga gtcacaacag cctgggatcc gccaccgcca g     41

<210> SEQ ID NO 48
<211> LENGTH: 34
<212> TYPE: DNA
<213> ORGANISM: Artificial
<220> FEATURE:
<223> OTHER INFORMATION: Primer

<400> SEQUENCE: 48
gaccatggcc caggctgttg tgactcagga atct      34

<210> SEQ ID NO 49
<211> LENGTH: 35
<212> TYPE: DNA
<213> ORGANISM: Artificial
<220> FEATURE:
<223> OTHER INFORMATION: Primer

<400> SEQUENCE: 49
cctccggagc ctaggacagt cagtctggtt cctcc       35

<210> SEQ ID NO 50
<211> LENGTH: 37
<212> TYPE: DNA
<213> ORGANISM: Artificial
<220> FEATURE:
<223> OTHER INFORMATION: Primer

<400> SEQUENCE: 50
gcggatccga tgtacagctt caggagtcag gacctgg      37

<210> SEQ ID NO 51
<211> LENGTH: 28
<212> TYPE: DNA
<213> ORGANISM: Artificial
<220> FEATURE:
<223> OTHER INFORMATION: Primer

<400> SEQUENCE: 51
cctggaaact gccgaatcca gttccagt          28

<210> SEQ ID NO 52

<211> LENGTH: 28
<212> TYPE: DNA
<213> ORGANISM: Artificial
<220> FEATURE:
<223> OTHER INFORMATION: Primer

<400> SEQUENCE: 52
actggaactg gattcggcag tttccagg                                    28

<210> SEQ ID NO 53
<211> LENGTH: 31
<212> TYPE: DNA
<213> ORGANISM: Artificial
<220> FEATURE:
<223> OTHER INFORMATION: Primer

<400> SEQUENCE: 53
gagcggccgc tgaggagact gtgagagtgg t                                31

<210> SEQ ID NO 54
<211> LENGTH: 40
<212> TYPE: DNA
<213> ORGANISM: Artificial
<220> FEATURE:
<223> OTHER INFORMATION: Primer

<400> SEQUENCE: 54
accagactga ctgtcctagg ctccggagga ggcggttcag                       40

<210> SEQ ID NO 55
<211> LENGTH: 41
<212> TYPE: DNA
<213> ORGANISM: Artificial
<220> FEATURE:
<223> OTHER INFORMATION: Primer

<400> SEQUENCE: 55
tcctgactcc tgaagctgta catcggatcc gccaccgcca g                     41

<210> SEQ ID NO 56
<211> LENGTH: 717
<212> TYPE: DNA
<213> ORGANISM: Unknown
<220> FEATURE:
<223> OTHER INFORMATION: scFv fragment Dx3860HL
<220> FEATURE:
<221> NAME/KEY: exon
<222> LOCATION: (1)..(717)

<400> SEQUENCE: 56

| gaa | gtg | aag | ctg | gtg | gag | tcc | ggg | gga | ggc | tta | gtg | aag | cct | gga | ggg | 48 |
| Glu | Val | Lys | Leu | Val | Glu | Ser | Gly | Gly | Gly | Leu | Val | Lys | Pro | Gly | Gly | |
| 1 | | | | 5 | | | | | 10 | | | | | 15 | | |

| tcc | ctg | aaa | ctc | tcc | tgt | gca | gcc | tct | gga | ttc | act | ttc | agt | tcc | tat | 96 |
| Ser | Leu | Lys | Leu | Ser | Cys | Ala | Ala | Ser | Gly | Phe | Thr | Phe | Ser | Ser | Tyr | |
| | | | 20 | | | | | 25 | | | | | 30 | | | |

| gcc | atg | tct | tgg | gtt | cgc | cag | act | cca | gag | aag | agg | ctg | gag | tgg | gtc | 144 |
| Ala | Met | Ser | Trp | Val | Arg | Gln | Thr | Pro | Glu | Lys | Arg | Leu | Glu | Trp | Val | |
| | | 35 | | | | | 40 | | | | | 45 | | | | |

| gca | tcc | ttt | agt | aat | ggt | ggt | atc | acc | tac | tat | cca | gac | agt | gtg | aag | 192 |
| Ala | Ser | Phe | Ser | Asn | Gly | Gly | Ile | Thr | Tyr | Tyr | Pro | Asp | Ser | Val | Lys | |
| | 50 | | | | | 55 | | | | | 60 | | | | | |

| ggc | cga | ttc | acc | atc | tcc | aga | gat | aat | gcc | agg | aac | atc | ctg | tac | ctg | 240 |
| Gly | Arg | Phe | Thr | Ile | Ser | Arg | Asp | Asn | Ala | Arg | Asn | Ile | Leu | Tyr | Leu | |
| 65 | | | | | 70 | | | | | 75 | | | | | 80 | |

| | | |
|---|---|---|
| caa atg acc agt ctg agg tct gag gac acg gcc att tat tac tgt gca<br>Gln Met Thr Ser Leu Arg Ser Glu Asp Thr Ala Ile Tyr Tyr Cys Ala<br>              85                    90                    95 | | 288 |
| aga ggc tat ggt cct gct tac tgg ggc caa ggt acc ctg gtc act gtc<br>Arg Gly Tyr Gly Pro Ala Tyr Trp Gly Gln Gly Thr Leu Val Thr Val<br>                  100                  105                110 | | 336 |
| tct tcc gga gga ggc ggt tca ggc gga ggt ggc tct ggc ggt ggc gga<br>Ser Ser Gly Gly Gly Gly Ser Gly Gly Gly Gly Ser Gly Gly Gly Gly<br>              115                  120                125 | | 384 |
| tcc cag gct gtt gtg act cag gaa tct gca ctc acc aca tca cct ggt<br>Ser Gln Ala Val Val Thr Gln Glu Ser Ala Leu Thr Thr Ser Pro Gly<br>        130                  135                140 | | 432 |
| gaa aca gtc aca ctc act tgt cgc tca agt act ggg gct gtt aca act<br>Glu Thr Val Thr Leu Thr Cys Arg Ser Ser Thr Gly Ala Val Thr Thr<br>145                  150                155                160 | | 480 |
| ctt aac tat gcc aac tgg gtc caa gaa aaa cca gat cat tta ttc act<br>Leu Asn Tyr Ala Asn Trp Val Gln Glu Lys Pro Asp His Leu Phe Thr<br>                  165                  170                175 | | 528 |
| ggt cta ata ggt aat acc aac aac cga gct cca ggt gtt cct gcc aga<br>Gly Leu Ile Gly Asn Thr Asn Asn Arg Ala Pro Gly Val Pro Ala Arg<br>        180                  185                190 | | 576 |
| ttc tca ggc tcc ctg att gga gac aag gct gcc ctc acc atc aca ggg<br>Phe Ser Gly Ser Leu Ile Gly Asp Lys Ala Ala Leu Thr Ile Thr Gly<br>                  195                  200                205 | | 624 |
| gca cag act gag gat gag gca ata tat ttc tgt gct cta tgg tac agc<br>Ala Gln Thr Glu Asp Glu Ala Ile Tyr Phe Cys Ala Leu Trp Tyr Ser<br>        210                  215                220 | | 672 |
| aac cat ttg gtg ttc ggt gga gga acc aaa ctg act gtc cta ggc<br>Asn His Leu Val Phe Gly Gly Gly Thr Lys Leu Thr Val Leu Gly<br>225                  230                235 | | 717 |

<210> SEQ ID NO 57
<211> LENGTH: 720
<212> TYPE: DNA
<213> ORGANISM: Unknown
<220> FEATURE:
<223> OTHER INFORMATION: scFv fragment Dx3860LH
<220> FEATURE:
<221> NAME/KEY: exon
<222> LOCATION: (1)..(720)

<400> SEQUENCE: 57

| | | |
|---|---|---|
| cag gct gtt gtg act cag gaa tct gca ctc acc aca tca cct ggt gaa<br>Gln Ala Val Val Thr Gln Glu Ser Ala Leu Thr Thr Ser Pro Gly Glu<br>1                    5                    10                    15 | | 48 |
| aca gtc aca ctc act tgt cgc tca agt act ggg gct gtt aca act ctt<br>Thr Val Thr Leu Thr Cys Arg Ser Ser Thr Gly Ala Val Thr Thr Leu<br>                  20                  25                30 | | 96 |
| aac tat gcc aac tgg gtc caa gaa aaa cca gat cat tta ttc act ggt<br>Asn Tyr Ala Asn Trp Val Gln Glu Lys Pro Asp His Leu Phe Thr Gly<br>                  35                  40                45 | | 144 |
| cta ata ggt aat acc aac aac cga gct cca ggt gtt cct gcc aga ttc<br>Leu Ile Gly Asn Thr Asn Asn Arg Ala Pro Gly Val Pro Ala Arg Phe<br>    50                  55                60 | | 192 |
| tca ggc tcc ctg att gga gac aag gct gcc ctc acc atc aca ggg gca<br>Ser Gly Ser Leu Ile Gly Asp Lys Ala Ala Leu Thr Ile Thr Gly Ala<br>65                  70                75                80 | | 240 |
| cag act gag gat gag gca ata tat ttc tgt gct cta tgg tac agc aac<br>Gln Thr Glu Asp Glu Ala Ile Tyr Phe Cys Ala Leu Trp Tyr Ser Asn<br>                  85                  90                95 | | 288 |
| cat ttg gtg ttc ggt gga gga acc aaa ctg act gtc cta ggc tcc gga<br>His Leu Val Phe Gly Gly Gly Thr Lys Leu Thr Val Leu Gly Ser Gly | | 336 |

```
gga ggc ggt tca ggc gga ggt ggc tct ggc ggt ggc gga tcc gaa gtg      384
Gly Gly Gly Ser Gly Gly Gly Gly Ser Gly Gly Gly Gly Ser Glu Val
            115                 120                 125 aag ctg gtg gag tcc ggg gga ggc tta gtg aag cct gga ggg tcc ctg      432
Lys Leu Val Glu Ser Gly Gly Gly Leu Val Lys Pro Gly Gly Ser Leu
130                 135                 140 aaa ctc tcc tgt gca gcc tct gga ttc act ttc agt cc tat gcc atg       480
Lys Leu Ser Cys Ala Ala Ser Gly Phe Thr Phe Ser Ser Tyr Ala Met
145                 150                 155                 160 tct tgg gtt cgc cag act cca gag aag agg ctg gag tgg gtc gca tcc      528
Ser Trp Val Arg Gln Thr Pro Glu Lys Arg Leu Glu Trp Val Ala Ser
                165                 170                 175 ttt agt aat ggt ggt atc acc tac tat cca gac agt gtg aag ggc cga     576
Phe Ser Asn Gly Gly Ile Thr Tyr Tyr Pro Asp Ser Val Lys Gly Arg
            180                 185                 190 ttc acc atc tcc aga gat aat gcc agg aac atc ctg tac ctg caa atg      624
Phe Thr Ile Ser Arg Asp Asn Ala Arg Asn Ile Leu Tyr Leu Gln Met
        195                 200                 205 acc agt ctg agg tct gag gac acg gcc att tat tac tgt gca aga ggc      672
Thr Ser Leu Arg Ser Glu Asp Thr Ala Ile Tyr Tyr Cys Ala Arg Gly
    210                 215                 220 tat ggt cct gct tac tgg ggc caa ggg act ctg gtc act gtc tct gca     720
Tyr Gly Pro Ala Tyr Trp Gly Gln Gly Thr Leu Val Thr Val Ser Ala
225                 230                 235                 240

<210> SEQ ID NO 58
<211> LENGTH: 729
<212> TYPE: DNA
<213> ORGANISM: Unknown
<220> FEATURE:
<223> OTHER INFORMATION: scFv fragment Dx3150HL
<220> FEATURE:
<221> NAME/KEY: exon
<222> LOCATION: (1)..(729)

<400> SEQUENCE: 58 gat gta cag ctt cag gag tca gga cct ggc ctc gtg aaa cct tct cag      48
Asp Val Gln Leu Gln Glu Ser Gly Pro Gly Leu Val Lys Pro Ser Gln
1               5                   10                  15 tct ctg tct ctc acc tgt tct gtc act ggc tac tcc atc acc agt ggc      96
Ser Leu Ser Leu Thr Cys Ser Val Thr Gly Tyr Ser Ile Thr Ser Gly
            20                  25                  30 ttt tac tgg aac tgg att cgg cag ttt cca gga aac aaa ctg gaa tgg     144
Phe Tyr Trp Asn Trp Ile Arg Gln Phe Pro Gly Asn Lys Leu Glu Trp
        35                  40                  45 atg ggc tac ata agc tac gac ggt tac aat aat tac aac cca ttt ctc     192
Met Gly Tyr Ile Ser Tyr Asp Gly Tyr Asn Asn Tyr Asn Pro Phe Leu
    50                  55                  60 aaa aat cga gtg tcc atc act cgt gac aca tct gag aac cag ttt ttc     240
Lys Asn Arg Val Ser Ile Thr Arg Asp Thr Ser Glu Asn Gln Phe Phe
65                  70                  75                  80 ctg aag ttg cat tct gtg act act gag gac aca gct aca tat tac tgt     288
Leu Lys Leu His Ser Val Thr Thr Glu Asp Thr Ala Thr Tyr Tyr Cys
                85                  90                  95 gta agt tac ggt agt cgg agg gga gtt acc tac tgg ggc caa ggt acc     336
Val Ser Tyr Gly Ser Arg Arg Gly Val Thr Tyr Trp Gly Gln Gly Thr
            100                 105                 110 act ctc aca gtc tcc tcc gga gga ggc ggt tca ggc gga ggt ggc tct     384
Thr Leu Thr Val Ser Ser Gly Gly Gly Gly Ser Gly Gly Gly Gly Ser
        115                 120                 125
```

```
ggc ggt ggc gga tcc cag gct gtt gtg act cag gaa tct gca ctc acc      432
Gly Gly Gly Gly Ser Gln Ala Val Val Thr Gln Glu Ser Ala Leu Thr
            130                 135                 140 aca tca cct ggt gaa aca gtc aca ctc act tgt cgc tca agt act ggg      480
Thr Ser Pro Gly Glu Thr Val Thr Leu Thr Cys Arg Ser Ser Thr Gly
145                 150                 155                 160 gct gtt aca act agt aac tat gcc aac tgg gtc caa gaa aaa cca gat      528
Ala Val Thr Thr Ser Asn Tyr Ala Asn Trp Val Gln Glu Lys Pro Asp
                165                 170                 175 cat tta ttc act ggt cta ata ggt aat acc aac aac cga gct cca ggt      576
His Leu Phe Thr Gly Leu Ile Gly Asn Thr Asn Asn Arg Ala Pro Gly
            180                 185                 190 gtt cct gcc aga ttc tct ggc tcc ctg att gga gac aag gct gcc ctc      624
Val Pro Ala Arg Phe Ser Gly Ser Leu Ile Gly Asp Lys Ala Ala Leu
        195                 200                 205 acc atc aca ggg gca cag act gag gat gag gcg ata tat ttc tgt gct      672
Thr Ile Thr Gly Ala Gln Thr Glu Asp Glu Ala Ile Tyr Phe Cys Ala
210                 215                 220 ctt tgg tac aac acc cat ttg gtg ttc ggt gga gga acc aga ctg act      720
Leu Trp Tyr Asn Thr His Leu Val Phe Gly Gly Gly Thr Arg Leu Thr
225                 230                 235                 240 gtc cta ggc                                                           729
Val Leu Gly <210> SEQ ID NO 59
<211> LENGTH: 732
<212> TYPE: DNA
<213> ORGANISM: Unknown
<220> FEATURE:
<223> OTHER INFORMATION: scFv fragment Dx3150LH
<220> FEATURE:
<221> NAME/KEY: exon
<222> LOCATION: (1)..(732)

<400> SEQUENCE: 59 cag gct gtt gtg act cag gaa tct gca ctc acc aca tca cct ggt gaa       48
Gln Ala Val Val Thr Gln Glu Ser Ala Leu Thr Thr Ser Pro Gly Glu
1               5                   10                  15 aca gtc aca ctc act tgt cgc tca agt act ggg gct gtt aca act agt       96
Thr Val Thr Leu Thr Cys Arg Ser Ser Thr Gly Ala Val Thr Thr Ser
            20                  25                  30 aac tat gcc aac tgg gtc caa gaa aaa cca gat cat tta ttc act ggt      144
Asn Tyr Ala Asn Trp Val Gln Glu Lys Pro Asp His Leu Phe Thr Gly
        35                  40                  45 cta ata ggt aat acc aac aac cga gct cca ggt gtt cct gcc aga ttc      192
Leu Ile Gly Asn Thr Asn Asn Arg Ala Pro Gly Val Pro Ala Arg Phe
50                  55                  60 tct ggc tcc ctg att gga gac aag gct gcc ctc acc atc aca ggg gca      240
Ser Gly Ser Leu Ile Gly Asp Lys Ala Ala Leu Thr Ile Thr Gly Ala
65                  70                  75                  80 cag act gag gat gag gcg ata tat ttc tgt gct ctt tgg tac aac acc      288
Gln Thr Glu Asp Glu Ala Ile Tyr Phe Cys Ala Leu Trp Tyr Asn Thr
                85                  90                  95 cat ttg gtg ttc ggt gga gga acc aga ctg act gtc cta ggc tcc gga      336
His Leu Val Phe Gly Gly Gly Thr Arg Leu Thr Val Leu Gly Ser Gly
            100                 105                 110 gga ggc ggt tca ggc gga ggt ggc tct ggc ggt ggc gga tcc gat gta      384
Gly Gly Gly Ser Gly Gly Gly Gly Ser Gly Gly Gly Gly Ser Asp Val
        115                 120                 125 cag ctt cag gag tca gga cct ggc ctc gtg aaa cct tct cag tct ctg      432
Gln Leu Gln Glu Ser Gly Pro Gly Leu Val Lys Pro Ser Gln Ser Leu
130                 135                 140
```

```
                                                     -continued tct ctc acc tgt tct gtc act ggc tac tcc atc acc agt ggc ttt tac    480
Ser Leu Thr Cys Ser Val Thr Gly Tyr Ser Ile Thr Ser Gly Phe Tyr
145                 150                 155                 160 tgg aac tgg att cgg cag ttt cca gga aac aaa ctg gaa tgg atg ggc    528
Trp Asn Trp Ile Arg Gln Phe Pro Gly Asn Lys Leu Glu Trp Met Gly
                165                 170                 175 tac ata agc tac gac ggt tac aat aat tac aac cca ttt ctc aaa aat    576
Tyr Ile Ser Tyr Asp Gly Tyr Asn Asn Tyr Asn Pro Phe Leu Lys Asn
            180                 185                 190 cga gtg tcc atc act cgt gac aca tct gag aac cag ttt ttc ctg aag    624
Arg Val Ser Ile Thr Arg Asp Thr Ser Glu Asn Gln Phe Phe Leu Lys
        195                 200                 205 ttg cat tct gtg act act gag gac aca gct aca tat tac tgt gta agt    672
Leu His Ser Val Thr Thr Glu Asp Thr Ala Thr Tyr Tyr Cys Val Ser
    210                 215                 220 tac ggt agt cgg agg gga gtt acc tac tgg ggc caa ggc acc act ctc    720
Tyr Gly Ser Arg Arg Gly Val Thr Tyr Trp Gly Gln Gly Thr Thr Leu
225                 230                 235                 240 aca gtc tcc tca                                                    732
Thr Val Ser Ser <210> SEQ ID NO 60
<211> LENGTH: 239
<212> TYPE: PRT
<213> ORGANISM: Unknown
<220> FEATURE:
<223> OTHER INFORMATION: Polypeptide encoded by scFv fragment Dx3860HL

<400> SEQUENCE: 60

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Phe Ser Asn Gly Gly Ile Thr Tyr Tyr Pro Asp Ser Val Lys
    50                  55                  60

Gly Arg Phe Thr Ile Ser Arg Asp Asn Ala Arg Asn Ile Leu Tyr Leu
65              70                  75                  80

Gln Met Thr Ser Leu Arg Ser Glu Asp Thr Ala Ile Tyr Tyr Cys Ala
            85                  90                  95

Arg Gly Tyr Gly Pro Ala Tyr Trp Gly Gln Gly Thr Leu Val Thr Val
        100                 105                 110

Ser Ser Gly Gly Gly Gly Ser Gly Gly Gly Gly Ser Gly Gly Gly Gly
    115                 120                 125

Ser Gln Ala Val Val Thr Gln Glu Ser Ala Leu Thr Thr Ser Pro Gly
130                 135                 140

Glu Thr Val Thr Leu Thr Cys Arg Ser Ser Thr Gly Ala Val Thr Thr
145                 150                 155                 160

Leu Asn Tyr Ala Asn Trp Val Gln Glu Lys Pro Asp His Leu Phe Thr
            165                 170                 175

Gly Leu Ile Gly Asn Thr Asn Asn Arg Ala Pro Gly Val Pro Ala Arg
        180                 185                 190

Phe Ser Gly Ser Leu Ile Gly Asp Lys Ala Ala Leu Thr Ile Thr Gly
    195                 200                 205

Ala Gln Thr Glu Asp Glu Ala Ile Tyr Phe Cys Ala Leu Trp Tyr Ser
210                 215                 220
```

Asn His Leu Val Phe Gly Gly Gly Thr Lys Leu Thr Val Leu Gly
225                 230                 235

<210> SEQ ID NO 61
<211> LENGTH: 240
<212> TYPE: PRT
<213> ORGANISM: Unknown
<220> FEATURE:
<223> OTHER INFORMATION: Polypeptide encoded by scFv fragment Dx3860LH

<400> SEQUENCE: 61

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Leu
            20                  25                  30

Asn Tyr Ala Asn Trp Val Gln Glu Lys Pro Asp His Leu Phe Thr Gly
        35                  40                  45

Leu Ile Gly Asn Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Leu Val Phe Gly Gly Gly Thr Lys Leu Thr Val Leu Gly Ser Gly
            100                 105                 110

Gly Gly Gly Ser Gly Gly Gly Ser Gly Gly Gly Ser Glu Val
        115                 120                 125

Lys Leu Val Glu Ser Gly Gly Gly Leu Val Lys Pro Gly Gly Ser Leu
    130                 135                 140

Lys Leu Ser Cys Ala Ala Ser Gly Phe Thr Phe Ser Ser Tyr Ala Met
145                 150                 155                 160

Ser Trp Val Arg Gln Thr Pro Glu Lys Arg Leu Glu Trp Val Ala Ser
                165                 170                 175

Phe Ser Asn Gly Gly Ile Thr Tyr Tyr Pro Asp Ser Val Lys Gly Arg
            180                 185                 190

Phe Thr Ile Ser Arg Asp Asn Ala Arg Asn Ile Leu Tyr Leu Gln Met
        195                 200                 205

Thr Ser Leu Arg Ser Glu Asp Thr Ala Ile Tyr Tyr Cys Ala Arg Gly
    210                 215                 220

Tyr Gly Pro Ala Tyr Trp Gly Gln Gly Thr Leu Val Thr Val Ser Ala
225                 230                 235                 240

<210> SEQ ID NO 62
<211> LENGTH: 243
<212> TYPE: PRT
<213> ORGANISM: Unknown
<220> FEATURE:
<223> OTHER INFORMATION: Polypeptide encoded by scFv fragment Dx3150HL

<400> SEQUENCE: 62

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Phe Tyr Trp Asn Trp Ile Arg Gln Phe Pro Gly Asn Lys Leu Glu Trp
        35                  40                  45

Met Gly Tyr Ile Ser Tyr Asp Gly Tyr Asn Asn Tyr Asn Pro Phe Leu 50                  55                  60
Lys Asn Arg Val Ser Ile Thr Arg Asp Thr Ser Glu Asn Gln Phe Phe
 65                  70                  75                  80

Leu Lys Leu His Ser Val Thr Thr Glu Asp Thr Ala Thr Tyr Tyr Cys
                 85                  90                  95

Val Ser Tyr Gly Ser Arg Arg Gly Val Thr Tyr Trp Gly Gln Gly Thr
                100                 105                 110

Thr Leu Thr Val Ser Ser Gly Gly Gly Gly Ser Gly Gly Gly Gly Ser
                115                 120                 125

Gly Gly Gly Gly Ser Gln Ala Val Val Thr Gln Glu Ser Ala Leu Thr
130                 135                 140

Thr Ser Pro Gly Glu Thr Val Thr Leu Thr Cys Arg Ser Ser Thr Gly
145                 150                 155                 160

Ala Val Thr Thr Ser Asn Tyr Ala Asn Trp Val Gln Glu Lys Pro Asp
                165                 170                 175

His Leu Phe Thr Gly Leu Ile Gly Asn Thr Asn Asn Arg Ala Pro Gly
                180                 185                 190

Val Pro Ala Arg Phe Ser Gly Ser Leu Ile Gly Asp Lys Ala Ala Leu
                195                 200                 205

Thr Ile Thr Gly Ala Gln Thr Glu Asp Glu Ala Ile Tyr Phe Cys Ala
210                 215                 220

Leu Trp Tyr Asn Thr His Leu Val Phe Gly Gly Gly Thr Arg Leu Thr
225                 230                 235                 240

Val Leu Gly

<210> SEQ ID NO 63
<211> LENGTH: 244
<212> TYPE: PRT
<213> ORGANISM: Unknown
<220> FEATURE:
<223> OTHER INFORMATION: Polypeptide encoded by scFv fragment Dx3150LH

<400> SEQUENCE: 63

Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
                35                  40                  45

Leu Ile Gly Asn Thr Asn Asn Arg Ala Pro Gly Val Pro Ala Arg Phe
            50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Asn Thr
                 85                  90                  95

His Leu Val Phe Gly Gly Gly Thr Arg Leu Thr Val Leu Gly Ser Gly
                100                 105                 110

Gly Gly Gly Ser Gly Gly Gly Ser Gly Gly Gly Ser Asp Val
                115                 120                 125

Gln Leu Gln Glu Ser Gly Pro Gly Leu Val Lys Pro Ser Gln Ser Leu
130                 135                 140

Ser Leu Thr Cys Ser Val Thr Gly Tyr Ser Ile Thr Ser Gly Phe Tyr
145                 150                 155                 160

Trp Asn Trp Ile Arg Gln Phe Pro Gly Asn Lys Leu Glu Trp Met Gly
                165                 170                 175

```
Tyr Ile Ser Tyr Asp Gly Tyr Asn Asn Tyr Asn Pro Phe Leu Lys Asn
            180                 185                 190

Arg Val Ser Ile Thr Arg Asp Thr Ser Glu Asn Gln Phe Phe Leu Lys
        195                 200                 205

Leu His Ser Val Thr Thr Glu Asp Thr Ala Thr Tyr Tyr Cys Val Ser
        210                 215                 220

Tyr Gly Ser Arg Arg Gly Val Thr Tyr Trp Gly Gln Gly Thr Thr Leu
225                 230                 235                 240

Thr Val Ser Ser

<210> SEQ ID NO 64
<211> LENGTH: 114
<212> TYPE: PRT
<213> ORGANISM: Unknown
<220> FEATURE:
<223> OTHER INFORMATION: Polypeptide of VH-chain variant (HL-M#5) of
      monoclonal antibody Dx 3860

<400> SEQUENCE: 64

Glu Val Lys Leu Val Glu Ser Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Asn Gly Gly Ile Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Thr Ser Leu Arg Ser Glu Asp Thr Ala Ile Tyr Tyr Cys Ala
                85                  90                  95

Arg Gly Tyr Gly Pro Ala Tyr Trp Gly Gln Gly Thr Leu Val Thr Val
            100                 105                 110

Ser Ser

<210> SEQ ID NO 65
<211> LENGTH: 114
<212> TYPE: PRT
<213> ORGANISM: Unknown
<220> FEATURE:
<223> OTHER INFORMATION: Polypeptide of VH-chain variant (LH-M#1) of
      monoclonal antibody Dx 3860

<400> SEQUENCE: 65

Glu Val Lys Leu Val Glu Ser Gly Gly Leu Val Arg Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Leu Ser Asn Gly Gly Ile Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Thr Ser Leu Arg Ser Glu Asp Thr Ala Ile Tyr Tyr Cys Ala
                85                  90                  95

Arg Gly Tyr Gly Pro Ala Tyr Trp Gly Gln Gly Thr Leu Val Thr Val
```

Ser Ala

<210> SEQ ID NO 66
<211> LENGTH: 114
<212> TYPE: PRT
<213> ORGANISM: Unknown
<220> FEATURE:
<223> OTHER INFORMATION: Polypeptide of VH-chain variant (LH-M#2) of
monoclonal antibody Dx 3860

<400> SEQUENCE: 66

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Val Ser Asn Gly Gly Ile Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Thr Ser Leu Arg Ser Glu Asp Thr Ala Ile Tyr Tyr Cys Ala
                85                  90                  95

Arg Gly Tyr Gly Pro Ala Tyr Trp Gly His Gly Thr Leu Val Thr Val
            100                 105                 110
```

Ser Ala

<210> SEQ ID NO 67
<211> LENGTH: 114
<212> TYPE: PRT
<213> ORGANISM: Unknown
<220> FEATURE:
<223> OTHER INFORMATION: Polypeptide of VH-chain variant (LH-M#3) of
nonoclonal antibody Dx 3860

<400> SEQUENCE: 67

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Leu Ser Asn Gly Gly Ile Thr Tyr Tyr Pro Asp Ser Val Lys
    50                  55                  60

Gly Arg Phe Thr Ile Ser Arg Asp Asn Ala Arg Asn Val Leu Tyr Leu
65                  70                  75                  80

Gln Met Thr Ser Leu Arg Ser Glu Asp Thr Ala Ile Tyr Tyr Cys Ala
                85                  90                  95

Arg Gly Tyr Gly Pro Ala Tyr Trp Gly Gln Gly Thr Leu Val Thr Val
            100                 105                 110
```

Ser Ala